(12) United States Patent
Fiorentino Gomez et al.

(10) Patent No.: US 8,734,863 B2
(45) Date of Patent: May 27, 2014

(54) **BIOACTIVE FRACTION OF *PETIVERIA ALLIACEA*, PHARMACEUTICAL COMPOSITION CONTAINING SAME, AND COMBINATION WITH IMMUNOSTIMULANTS FOR TREATING CANCER**

(75) Inventors: Susana Fiorentino Gomez, Bogotá (CO); María Claudia Cifuentes Barreto, Bogotá (CO); John Freddy Hernandez Montaño, Bogotá (CO); Sandra Paola Santander Gonzales, Bogotá (CO); Claudia Patricia Urueña Pinzon, Bogotá (CO); Diana Mercedes Castañeda Uvajoa, Bogotá (CO)

(73) Assignee: Pontificia Universidad Javeriana, Bogota (CO)

( * ) Notice: Subject to any disclaimer, the term of this patent is extended or adjusted under 35 U.S.C. 154(b) by 0 days.

(21) Appl. No.: 13/499,798

(22) PCT Filed: Sep. 22, 2010

(86) PCT No.: PCT/IB2010/002504
§ 371 (c)(1),
(2), (4) Date: Aug. 2, 2012

(87) PCT Pub. No.: WO2011/039629
PCT Pub. Date: Apr. 7, 2011

(65) Prior Publication Data
US 2012/0294897 A1    Nov. 22, 2012

(30) Foreign Application Priority Data

Oct. 2, 2009   (CO) ........................................ 108636

(51) Int. Cl.
*A61K 36/28*   (2006.01)
(52) U.S. Cl.
USPC ....................................... 424/725; 424/195.15
(58) Field of Classification Search
USPC ......................................................... 424/725
See application file for complete search history.

(56) References Cited

U.S. PATENT DOCUMENTS 8,334,316 B2 *  12/2012  Xu et al. ........................ 514/438
2005/0261321 A1 *  11/2005  Xu et al. ........................ 514/269

(Continued)

FOREIGN PATENT DOCUMENTS

WO     WO 2008/118874     10/2008

OTHER PUBLICATIONS

Uruena et al, BioMed Complementary and Alternative Medicine, vol. 8(60), pp. 1-17, Nov. 18, 2008.*

(Continued)

*Primary Examiner* — Albert Navarro
*Assistant Examiner* — Ginny Portner
(74) *Attorney, Agent, or Firm* — Merchant & Gould P.C.

(57) ABSTRACT

The invention relates to a bioactive fraction of *Petiveria alliacea* having an antitumour activity, and to the use of same for producing medicaments for treating cancer. The invention also relates to a pharmaceutical combination for treating, comprising the bioactive fraction of *Petiveria alliacea* and at least one immunostimulant that can produce the phenotypic and/or functional maturation of the dendritic cells. The invention further relates to sequential administration of the bioactive fraction of *Petiveria alliacea* or the composition containing same and immunostimulant agent.

9 Claims, 17 Drawing Sheets

(56) References Cited

U.S. PATENT DOCUMENTS

| | | | |
|---|---|---|---|
| 2007/0104728 A1* | 5/2007 | Olalde Rangel | 424/195.15 |
| 2008/0063658 A1* | 3/2008 | Olalde Rangel | 424/195.15 |
| 2008/0070839 A1* | 3/2008 | Williams et al. | 514/12 |
| 2008/0081046 A1* | 4/2008 | Olalde | 424/195.15 |
| 2008/0089946 A1* | 4/2008 | Olalde Rangel | 424/548 |
| 2008/0118582 A1* | 5/2008 | Olalde Rangel | 424/726 |
| 2010/0119629 A1* | 5/2010 | Olalde Rangel | 424/726 |
| 2011/0052718 A1* | 3/2011 | Rangel | 424/549 |

OTHER PUBLICATIONS

De Lima, Thereza C. et al, Mem. Inst. Oswaldo Cruz, Rio de Janeiro, vol. 86, Suppl. II, pp. 153-158, 1991, Evaluation of antinociceptive effect of *Petiveria alliacea* (guine) in animals.*

Nata-Greenwood, Eugenia et al, Anticancer Research, vol. 21, pates 1763-1770, 2001, Discovery of Novel Inducers of Cellular Differentiation Using HL-60 Promyelocytic Cells.*

Gomes, Patricia B et al, Journal of Ethnopharmacology, vol. 120, (2008), pp. 209-214, Central effects of isolated fractions from the root of *Petiveria alliacea* L (tipi) in mice, available online Aug. 19, 2008.*

International Search Report for International Application No. PCT/IB2010/002504 mailed Apr. 18, 2011, pp. 1-8.

American Cancer Society Handout. *Cancer Facts & Figures*. 2007. 56 pages.

Costa et al. "Screening in mice of some medicinal plants used for analgesic purposed in the state of São Paulo Part II." *J. of Ethnopharm.* vol. 27. 1986. pp. 25-33.

Dai et al. "T-Cell-Immunity-Based Inhibitory Effesc of Orally administered herbal medicine juzen-taiho-to on the growth of primarily developed melanocytic tumors in RET-transgenic mice." *Society for Investigative Dermatology.* vol. 117. No. 3. 2001. pp. 694-701.

De Lima et al. "Evaluation of Antinociceptive effect of *Petiveria allacea* (guine) in animals." *Mem. Ins.* vol. 86. Suppl. II. 1991. pp. 153-158.

De Sousa et al. "Dibenzyl Trisulphide and Trans-N-Methyl-4-methoxyproline from *Petiveria alliacea*." *Phytochem.* vol. 29. No. II. 1990. pp. 3653-3655.

Delle Monache et al. "6-C-Formyl and 6-C-Hydroxymethyl Flavanones from *Petiveria alliacea*." *Phytochem.* vol. 31. No. 7. 1992. pp. 2481-2482.

Delle Monache et al. "*Petiveria alliacea* II: Further Flavonoids and Triterpenes." *Gazette Chemica Italiana*. vol. 126. 1996. pp. 275-278.

Firenzuli et al. "The Medicinal Mushroom *Agaricus blazei* Murrill: Review of Literature and Pharmaco-Toxicological Problems." *eCAM* vol. 5. No. I. 2008. pp. 3-15.

Israilides et al. "In Vitro cytostatic and immunomodulatory properties of the medicinal mushroom *Lentinula edodes.*" *Phytomedicine.* vol. 15. 2008. pp. 512-519.

Kanazawa et al. "Effect of PSK on the maturation of dendritic cells derived from human peripheral blood monocytes." *Immunology Letters.* vol. 91. 2004. pp. 229-238.

Kato et al. "The Herbal Medicine Sho-saiko-to Inhibits Growth an dMetastatsis of Malignant Melanoma Primarily Developed in ret-Transgenic Mice." *The Society for Investigative Dermatology.* vol. 111. No. 4. 1998. pp. 640-644.

Kim et al. "Effect of water-soluble proteoglycan isolated from *Agaricus blazei* on the maturation of murine bone marrow-derived dendritic cells." *International Immunopharm.* vol. 5. 2005. pp. 1523-1532.

Kim et al. "Partial Characterization and immunostimulatory Effect of a Novel Polysaccharide-Protein Complex Extracted from *Phellinus linteus.*" *Biosci. Biotenol. Biochem.* vol. 70. No. 5 2006. pp. 1218-1226.

Kim et al. "Water Extract of Cordyceps militarious Enhances Maturation of Murine Bone Marrow-Derived Dendritic Cells in Vitro." *Biol. Pharm. Bull.* vol. 29. No. 2. 2006. pp. 354-360.

Kubec et al. "Cysteine sulfoxide derivatives in *Petriveria alliacea.*" *Phytochem.* vol. 58. 2001. pp. 981-985.

Kubec et al. "S-Substituted cysteine derivatives and thiosulfinate formation in *Petiveria alliacea*—part II." *Phytochem.* vol. 61. 2002. pp. 675-680.

Kubec et al. "γ-Glutamyl dipeptides in *Petiveria alliacea.*" *Phytochem.* vol. 66. 2005. pp. 2494-2497.

Li et al. "Quality control of *Cordyceps sinensis*, a valued traditional Chinese medicine." *J. of Pharm and Biomed. Analysis.* vol. 41. 2006. pp. 1571-1584.

Liang et al. "Quality control of herbal medicines." *J. of Chromatography.* vol. 812. 2004. pp. 53-70.

Lin et al. "Polysaccharide purified from *Ganoderma lucidum* induced activation and maturation of human monocyte-derived dendritic cells by the NF-kB and p38 mitogen-activated protein kinase pathways." *J. of Leukocyte Bio.* vol. 78. 2005. pp. 533-543.

Lopes-Martins et al. "The anti-inflammatory and analgesic effects of a crude extract of *Petiveria alliacea* L. (Phytolaccaceae)." *Phytomed.* vol. 9. 2002. pp. 245-248.

Marie et al. "Drug resistance in hematologic malignancies." *Current Opinion in Oncology.* vol. 13. 2001. pp. 464-469.

Morales et al. "Preliminary screening of five ethnomedicinal plants of Guatemala." *Il Farmaco.* vol. 56. 2001. pp. 523-526.

Ng. "Review: A review of research on protein-bound polysaccharide (polysaccharopeptide, psp) from the mushroom *Coriolus versicolor* (basidiomycetes: polyporaceae)." *Gen. Pharmac.* vol. 30. No. 1. 1998. pp. 1-4.

Park et al. "Acidic polysaccharides isolated from *Phellinus linteus* induce phenotypic and functional maturation of murine dendritic cells." *Biochem. and Biophys. Res. Comm.* vol. 312. 2003. pp. 449-458.

Rosi et al. "Antiproliferative effects of *Petiveria alliacea* on several tumor cell lines." *Pharm. Res.* vol. 22. Sep. 1990. pp. 434.

Rosner et al. "Disassembly of microtubules and inhibition of neurite outgrowth, neuroblastoma cell proliferation, and MAP kinase tyrosine dephosphorylation by dibenzyl trisulphide." *Biochem et Biophys Acta.* vol. 1540. 2001. pp. 166-177.

Santandar et al. "Differential gene expression tumor cells induced by *Petiveria alliacia* treatment." *Univ. Med. Bogota.* vol. 50. No. 3. 2009. pp. 284-296. English Abstract provided.

Shao et al. "Regulation on maturation and function of dendritic cells by *Astragalus mongholicus* polysaccharides." *Int. Immunopharm.* vol. 6. 2006.pp. 1161-1166.

Shimizu et al. "An Acidic Polysaccharide Having Activity on Reticuloendothelial System from the Root of *Astragalus mongholicus.*" *Chem. Pharm. Bull.* vol. 39. No. 11. 1991. pp. 2969-2972.

Uruena et al. "*Petiveria alliacea* extracts uses multiple mechanisms to inhibit growth of human mouse tumoral cells." *BioMed Chentral BMC Compl. & Alt. Med.* vol. 8, No. 1. Nov. 18, 2008. pp. 60.

Wang et al. "The anti-tumor effect of *Ganoderma lucidum* is mediated by cytokines released from activated macrophages and t lymphocytes." *Int. J. Cancer.* vol. 70. 1997. pp. 699-705.

Wang et al. "Isolation and Structural Analysis of an Acidic Polysaccharide from *Astragalus membranaceus* (Fisch.) Bunge." *J. of Integrative Plant Biol.* vol. 48.No. 11. 1379-1384, 2006.

Williams et al. "A Critical Review of the Therapeutic Potentioal of Dibenzyl Trisulphide Isolated from *Petriveria alliacea* L (Guinea hen weed, anamu)." *West Indian Med. J.* vol. 56. No. 1. 2007. pp. 17-21.

Xie et al. "Chromatographic fingerprint analysis—a rational approach for quality assessment of traditional Chinese herbal medicine." *J. of Chrom.* vol. 1112. 2006. pp. 171-180.

Bates et al., "Insulin-like effect of pinitol", British Journal of Pharmacology, 2000, vol. 130, pp. 1944-1948.

* cited by examiner a. CD86 expression b. HLA-DR expression

BIOACTIVE FRACTION OF *PETIVERIA ALLIACEA*, PHARMACEUTICAL COMPOSITION CONTAINING SAME, AND COMBINATION WITH IMMUNOSTIMULANTS FOR TREATING CANCER

This application is a National Stage Application of PCT/IB2010/002504, filed 22 Sep. 2010, which claims benefit of Serial No. 09-108636, filed 2 Oct. 2009 in Colombia and which applications are incorporated herein by reference. To the extent appropriate, a claim of priority is made to each of the above disclosed applications.

FIELD OF THE INVENTION

State of the Art

Cancer occurs when the mechanisms maintaining cell normal growth rate are disturbed and generate excessive cell division. Genome mutation are the principal alterations occurring frequently in the genome of any cell in the body, inducing cellular transformation that can generate a malignant tumor able to invade adjacent normal tissue and to metastasize. In the process of malignant transformation, some tumor cells develop simultaneous resistance to multiple cytotoxic drugs (Cooper G. 2004), Cooper, G. 2007. *The cell: A molecular approach. Tercera edición. Capitulo* 15: 631-667 so the search for new antitumor compounds is an area of interest.

The tumors are classified according to the cell type they were generated, being the carcinomas (epithelial cell generated), the more frequent, followed by sarcomas (solid tumors) and leukemias or lymphomas (cells of hematopoietic origin) (Cooper G. 2004).

Despite the efforts made in experimental and clinical research programs, mortality from cancer remains extremely high. According to the American Cancer Society statistics, cancer is the second cause of death in the U.S.—564,830 deaths/year—placed just below cardiovascular diseases (American Cancer Society; 2007). With currently available treatments one third of the patients without metastasis are relieved, however, in the remaining cases the early micrometastases is a feature of the neoplasm, indicating the requirement for a systemic approach such as chemotherapy (often in conjunction with surgery or radiation) for the effective control of cancer.

More than 100 drugs are currently used in chemotherapy and can be classified depending on the molecular target upon which exerts its therapeutical activity, for example, drugs that generate DNA crosslinking (cisplatin), DNA alkylation (dacarbazine), microtubules disruption (taxol, vinblastine), membranes disruption (doxorubicin), topoisomerase inhibitors (etoposide, topotecan) or also structural analogs (methotrexate). Despite this great diversity of medicaments, tumor cells develop resistance to multiple drugs generating a considerable reduction in the expected clinical response to the pharmacological therapy.

Multiple mechanisms have been implicated in the development of single target drug resistance, as the overexpression of ABC superfamily transporters, the expression of enzymes modifiers, or the faults on the apoptosis induction after chemotherapy (Marie, Jean-Pierre, 2001). Marie J P. 2001. *Drug resistance in hematologic malignancies. Curr Opin Oncol* 13: 463-469. The development of new antitumor agents with several molecular targets, could allow to overcome the resistance mechanisms of tumor cells. Natural products can be the source of new compounds with different mechanisms of action and might be a therapeutic alternative being the raw material for the standardization of complex extracts that provide a synergistic effect and ensure the activity on multiple molecular targets simultaneously.

Two factors are important in the elimination of tumors: (1) tumor cell destruction without adverse effects on normal cells and (2) generation of an immune response following treatment, capable of removing the residual tumor cells. The use of a treatment method that in addition to inducing the death tumor enables subsequent control of residual tumor proliferation is an improvement in antitumor therapy. Some herbal supplements made from plants used in traditional Oriental medicine, such as Sho-Saiko-to and Juzen-taiho-to induce death by inhibiting tumor metastasis and subsequently allow the generation of an antitumor response (Kato M, et al. "*The herbal medicine Sho-saiko-to inhibits growth and metastasis of malignant melanoma primarily developed in ret-transgenic mice.*" J Invest Dermatol 1998, 111:640-4.; Dai Y, et al "*T-cell-immunity-based inhibitory effects of orally administered herbal medicine juzen-taiho-to on the growth of primarily developed melanocytic tumors in RET-transgenic mice.*" J Invest Dermatol 2001, 117:694-701.). Within these herbal preparations have been partially characterized the compounds responsible for killing tumor but not studied the type of death suffered by tumor cells or compounds have been clearly identified activators of dendritic cells (DC).

Effective antitumor therapy must take into account not only the death of the tumors, but the kind of death they will suffer. Although death by apoptosis is the most studied, is well known that the transfer of tumor antigens to DCs occurs more efficiently if the death follows a cellular stress, which causes increased heat shock proteins involved in the cross sensitization process to the DC allowing the activation of cytotoxic T lymphocytes. Death by apoptosis and late necrosis could be one of the best ways to kill tumors.

*Petiveria alliacea* Linn is a perennial herb of the Phytolaccaceae family widely known in traditional medicine in the countries of Central and South America, the Caribbean and Africa (Lopes-Martins R A, et al. "*The anti-inflammatory and analgesic effects of a crude extract of Petiveria alliacea L. (Phytolaccaceae).*" Phytomedicine 2002, 9:245-8). Traditionally, infusion of the leaves and cooking or root powder have been used in the treatment of various diseases, because its antispasmodic, antirheumatic, antiinflammatory (Lopes-Martins R A, et al. "*The anti-inflammatory and analgesic effects of a crude extract of Petiveria alliacea L. (Phytolaccaceae).*" Phytomedicine 2002, 9:245-8; Morales C, et al "*Preliminary screening of five ethnomedicinal plants of Guatemala.*" Farmaco 2001, 56:523-526.), antinociceptive (Di Stasi L C, et al. "*Screening in mice of some medicinal plants used for analogesic purposes in the state of Sao Paulo.*" J Ethnopharmacol 1988, 24:205-11.), hypoglycemic and abortifacient (De Lima T C, et al "*Evaluation of antinociceptive effect of Petiveria alliacea (Guine) in animals.*" Mem Inst Oswaldo Cruz 1991, 86 (Suppl 2):153-8; De Sousa P J, "*Guiné: erva medicinal ou tóxica.*" Ciênc Cult 1987, 39:645-646.). In some countries of Central and South America aqueous and alcoholic infusions have been used to treat leukemias and breast cancer with good results (Gupta M., "*Petiveria alliacea in 270 plantas medicinales iberoamericanas*", Presencia ed edn 1995.; Garcia B: "*Flora medicinal de Colombia,*" Imprenta nacional ed. Bogotá edn. Bogotá 1974).

Different compounds have been isolated and reported for *P. alliacea* including flavonoids such as astilbina, miricitrina and engeletina; triterpenes such as acid barbinérvico and α-friedelinol; lipids as lignoceric acid, nonadecanoic acid and oleic acid; other compounds such as allantoin, coumarin, daucosterol (De Sousa J R, et al. *"Dibenzyl trisulphide and trans-N-methyl-4-methoxyproline from Petiveria alliacea." Phytochemistry* 1990, 29:3653-3655. Delle-Monache F, et al: *"II. Further Flavonoids and Triterpenes". Gazzeta Chimica Italiana* 1996, 126:275-278. Delle-Monache F, Cuca L E: *"6-C-formyl and 6-C hidroxymethyl flavonones from Petiveria alliacea." Phytochemistry* 1992, 31:2481-2482) various dipeptides glutamic (Kubec R, et al. *"Gamma-Glutamyl dipeptides in Petiveria alliacea." Phytochemistry* 2005, 66:2494-7), sulfur containing amino acids such as S-benzyl cysteine sulfoxide and S-(2-hydroxyethyl)-cysteine sulfoxide (Kubec R, et al. *"Cysteine sulfoxide derivatives in Petiveria alliacea." Phytochemistry* 2001, 58:981-5. Kubec R, et al. *"S-Substituted cysteine derivatives and thiosulfinate formation in Petiveria alliacea-part II." Phytochemistry* 2002, 61:675-80) and the dibenzyl trisulfide (DTS) a lipophilic compound having immunomodulatory (Rosner H, et al. *"Disassembly of microtubules and inhibition of neurite outgrowth, neuroblastoma cell proliferation, and MAP kinase tyrosine dephosphorylation by dibenzyl trisulphide." Biochim Biophys Acta* 2001, 1540:166-77) and cytotoxic activity associated with the cytoskeleton (Williams L A, et al. *A critical review of the therapeutic potential of dibenzyl trisulphide isolated from Petiveria alliacea L(guinea hen weed, anamu). West Indian Med J* 2007, 56:17-21). Although the DTS showed good cytotoxic activity, its high toxicity even affect normal cells has not allowed its use in clinical and therapeutic (Williams L A, et al. *A critical review of the therapeutic potential of dibenzyl trisulphide isolated from Petiveria alliacea L(guinea hen weed, anamu). West Indian Med J* 2007, 56:17-21).

The present invention discloses a bioactive fraction of *Petiveria alliacea*, which induces cell death by different ways: acts on the cytoskeleton by inducing cell cycle arrest in G2 phase, and then induces apoptosis by mechanisms mitochondria dependent or independent, related to the polarity of the fraction. The complexity of the fractions of this invention also allows the induction of cellular stress altering the HSP70 inducible expression, generating the senescence of a part of the cell population, allowing the amplification of the immune response. Therefore, the biological activity of the fractions of the invention on multiple molecular targets of tumor cells, opens the possibility of overcoming the mechanisms of drug resistance developed by tumor cells.

The induction of immune response depends on several factors; among these cell debris generated during apoptosis and necrosis have been reported as source of antigen that can be phagocytosed by DC (professional antigen presenting cells) to activate immune system. In the present invention, we ensure that the immature dendritic cell can phagocytose and process tumor antigens, which is made of a less efficient manner by an activated cell. Subsequently induction of dendritic cell activation, with an immunostimulant, used in this antitumor treatment, allows the antigen presentation to T cells and the generation of an effective immune response. The benefits of this type of therapy are to ensure that once the tumor cell is destroyed, DC can be fully activated, to avoid the tolerance induction and the write activation of an effector immune response.

Based on the presented above, the present invention shows a method of treatment for the elimination of tumor cells via the administration of a bioactive fraction *Petiveria alliacea* with antitumor activity on multiple cellular targets and on the other hand, activating antigen-presenting DC, which have phagocytized remnants of tumor cells in vivo by administration of an immunostimulant agent. This dual therapy allows the destruction of the tumor and subsequently, the activation of tumor specific immune response by a cross-sensitization mechanism.

Likewise, the invention provides a pharmaceutical composition for treating cancer comprising a bioactive fraction *Petiveria alliacea* with antitumor activity and at least one or more pharmaceutically acceptable excipients. Such composition may be administered separately or as part of a combination for treating cancer comprising the composition defined previously and one or more immunostimulatory agents capable of inducing phenotypic and/or functional maturation of DC.

OBJECTS OF THE INVENTION

In a first objective, the invention is related to a bioactive fraction of *Petiveria alliacea* obtained by bioguided procedures, standardized and analytically marked for treating cancer.

In a second objective, the invention describes a pharmaceutical composition for treating cancer comprising the bioactive fraction of *Petiveria alliacea* and at least one or more pharmaceutically acceptable excipients.

In a third objective, the invention describes a pharmaceutical combination for treating cancer, comprising the bioactive fraction of *Petiveria alliacea* or a pharmaceutical composition containing same and at least one immunostimulant agent that can produce the phenotypic and/or functional maturation of the dendritic cells.

Additionally, is part of the invention the use of said fraction in drug product manufacture for treating cancer and a treatment kit comprising a pharmaceutical composition containing the bioactive fraction of *Petiveria alliacea* and at least one or more pharmaceutically acceptable excipients, a composition containing one or more immunostimulant agents that can produce the phenotypic and/or functional maturation of the dendritic cells and at least one or more pharmaceutically acceptable excipients and optionally instructions for use.

Finally, the invention describes a method for treating cancer comprising sequential administration of an effective therapeutically amount of the bioactive fraction of *Petiveria alliacea* or the composition containing same and, in a time between 24 hours and 2 weeks, administration of an effective therapeutically amount of at least one immunostimulant agent that can produce the phenotypic and/or functional maturation of the dendritic cells.

DETAILED DESCRIPTION OF THE INVENTION

Figure 1:
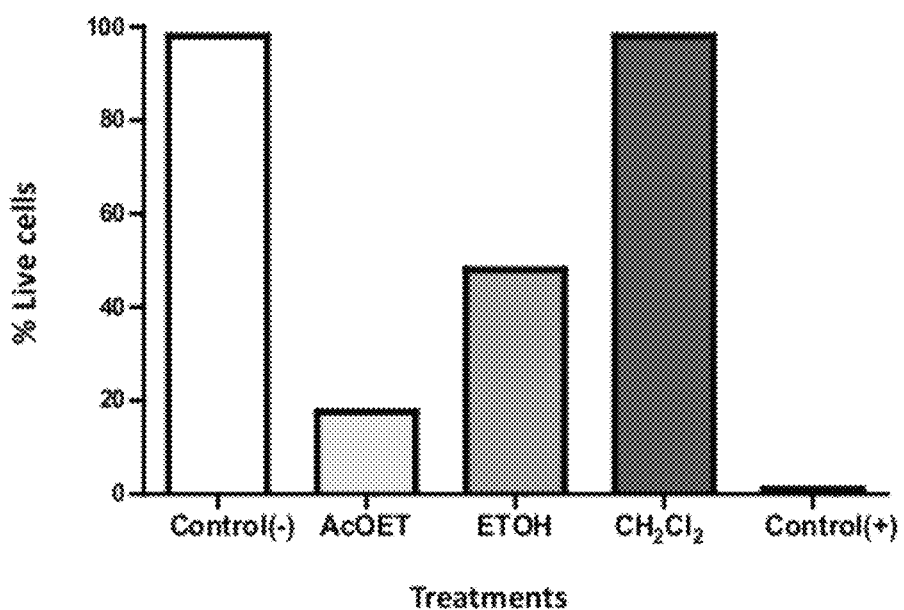
FIG. 1 shows the NB4 tumor cell line viability treated with a *Petiveria alliacea* extracts obtained with ethanol, ethyl acetate and dichloromethane.

The expression "immunostimulant agent" means an agent that can produce the phenotypic (CD86 and HLA-DR increase) and/or functional maturation of the dendritic cells (TNF-α production). Examples specially considering in the scope of the invention are polysaccharides and/or glycopeptides obtained from: *Ganoderma lucidum, Astragalus membranaceus, Grifola frondosa, Phellinus linteus, Cordyceps militaris, Lentinus edodes, Coriolus versicolor, Agaricus blazei* or *Petiveria alliacea*.

The expression "standardized bioactive fraction" means a fraction or active molecules complex mix with biological activity obtained from *Petiveria alliacea* by classical separation procedures that included plant material maceration, heat reflux extraction and analytical, semi-preparative or preparative chromatography. Standardization of herbal preparations required the implementation of good agriculture and manufacture practices since qualitative and quantitative composition could change by plant related factors (i.e. climatic conditions, harvest and collection practices) and extraction procedures. World Health Organization Guidelines on Good Manufacturing Practices (GMP) for Herbal Medicines established the chromatographic fingerprint obtained by modern analytical techniques (GC, HPLC and HPTLC) as a tool to quality control and standardization of herbal preparations (World Health Organization, Geneva 2007). This pattern shows a complete picture of the proportion of analytes, which allow a qualitative and quantitative approximation to authenticate herbal material, quality assurance and measure stability of herbal preparations (Peishan Xie. 2006). Fingerprint analyses is perform through multivariate chemometrics analysis evaluating similarity (correlation and congruence coefficients) and pattern recognition methods such as k-nearest neighbor—KNN—and soft independent modeling of class analogy—SIMCA—(Liang Y., Xie P., Chan K., 2004).

The expression "bioactive fraction of *Petiveria alliacea* obtained by bioguided procedures" means a semi-processed extract obtained by a directed rational procedure since an herbal material crude extract using biological assays like criteria to screen and selection of fractions.

The expression "bioactive fraction analytically marked" means a bioactive fraction in which their components have been quantificated by chromatographic technics using internal or external markers compounds.

The expression "sequential administration" means the administration of two or more pharmaceutical compositions of the antitumoural bioactive fraction of *Petiveria alliacea* and an immunostimulant agent, in a time between 24 hours and 2 weeks, preferably between 72 and 192 h. The sequential administration allows tumor cell phagocytosis by immature dendritic cells.

The expression "simultaneous administration" means the coadministration of a pharmaceutical composition of the antitumoural bioactive fraction of *Petiveria alliacea* and a conventional drug product use in chemotherapy.

The expression "effective therapeutically amount" means the appropriate dose level of drugs or bioactive fractions that produce the biological effect in a favor risk/benefit balance.

The expression "therapeutic" include prophylaxis and treatment of diseases in mammals including humans.

The invention presents biologically active fractions—bioactive fractions—obtained from *Petiveria alliacea* by classical procedures through bioguided focus. Standardized fractions are complex mixes and were named according to extraction and purification procedure as FAST, F4 and S3 fraction. To obtain bioactive fractions the herbal material was cleaning, dry and ground until particle size required.

*Petiveria alliacea* crude extracts in organic solvents (ethanol, ethyl acetate and dichloromethane) were obtained and biological evaluated over tumour cell lines. Example 1 (FIG. 1) shows clearly that ethyl acetate extract induce higher cytotoxicity over NB4 tumor cells compare to ethanolic (which has been commonly use and obtained by different laboratories) and dichloromethane.

Since these results, ethyl acetate extract were selected as matrix to obtain fractions. FAST bioactive fraction was obtained by extraction in ethanol (5 L/Kg) at room temperature (15° C.) during 10 days with solvent recirculation twice a day and concentrated under reduced pressure. The dry extract was fractionated with ethyl acetate at room temperature (15° C.), concentrate, adsorbed over sea sand purified (particle size 0.1-0.3 mm Merck®) and finally extracted with $MeOH:H_2O$ 7:3.

F4 bioactive fraction was obtained by reflux extraction in ethanol, filtration and evaporation, liquid-liquid extraction in ethyl acetate, drying and separation using RP-18 and mobile phase MeOH—H2O (1:1, 7:3 and 9:1). One of the fractions eluted in MeOH—H2O 7:3 were named F4.

S3 bioactive fraction was obtained by Soxhlet extraction in ether (4 L), dichloromethane, ethyl acetate and ethanol 96% over 48 h. Extracts were filtrated and evaporated until dryness. Ethyl acetate extract was flocculated with $EtOH:H_2O$ 1:1 and was heated at 65° C. during 20 min. The supernatant was recovered and percolated through silica gel G-60 with dichloromethane, ethyl acetate and ethanol 96%. Ethyl acetate fraction was recovered and fractionated through a silica gel G-60 column and eluted with dichloromethane: ethyl acetate (7:3, 1:1), ethyl acetate and ethanol 96%. Fraction named S3 corresponds to fraction eluted with solvent system dichloromethane: ethyl acetate (7:3).

Figure 2:
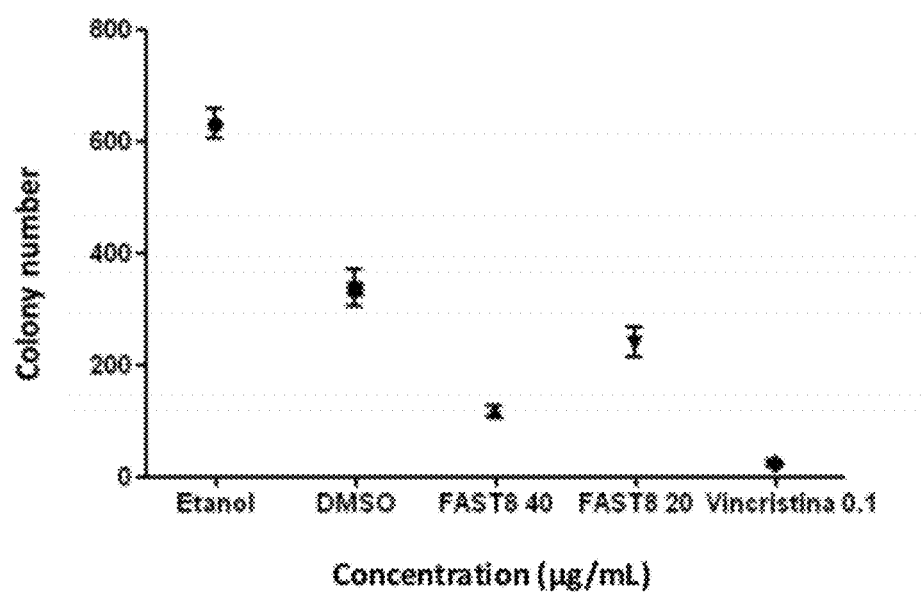
FIG. 2 shows the effect of FAST bioactive fraction of *Petiveria alliacea* over 4T1 cell line clonogenic capacity.
Figure 3:
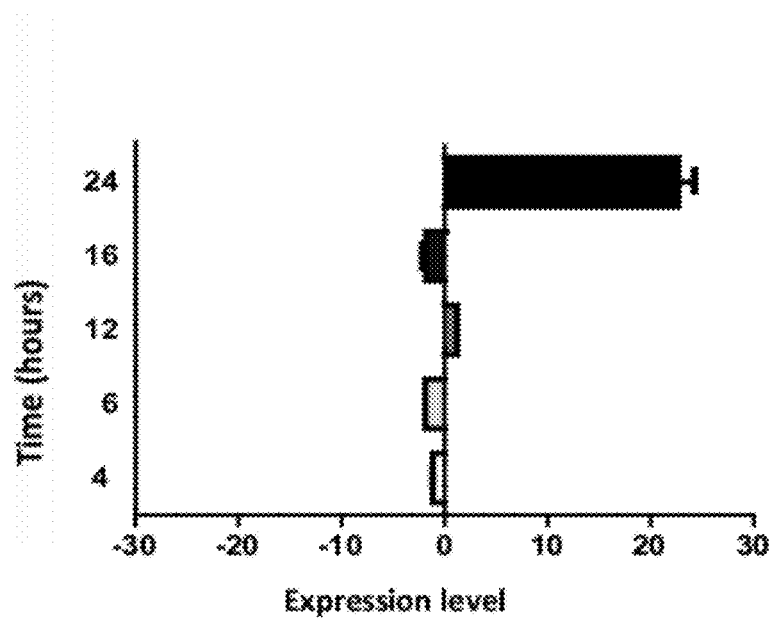
FIG. 3 presents the pyruvate kinase mRNA increase in 4T1 cell line treated with FAST bioactive fraction of *Petiveria alliacea*.
Figure 4:
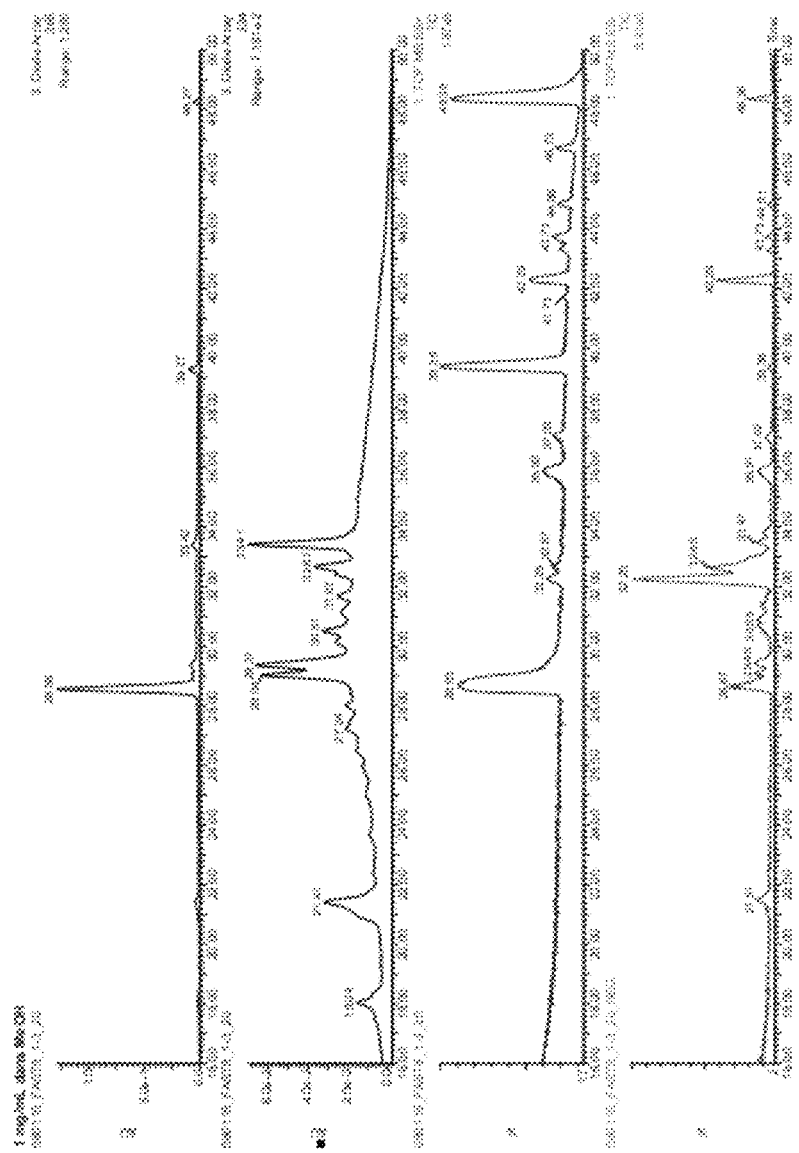
FIG. 4 presents the MS of FAST bioactive fraction of *Petiveria alliacea* obtained in a liquid chromatography time-of-flight mass spectrometry (LC-TOF-MS) in both positive and negative ESI modes.
Figure 5:
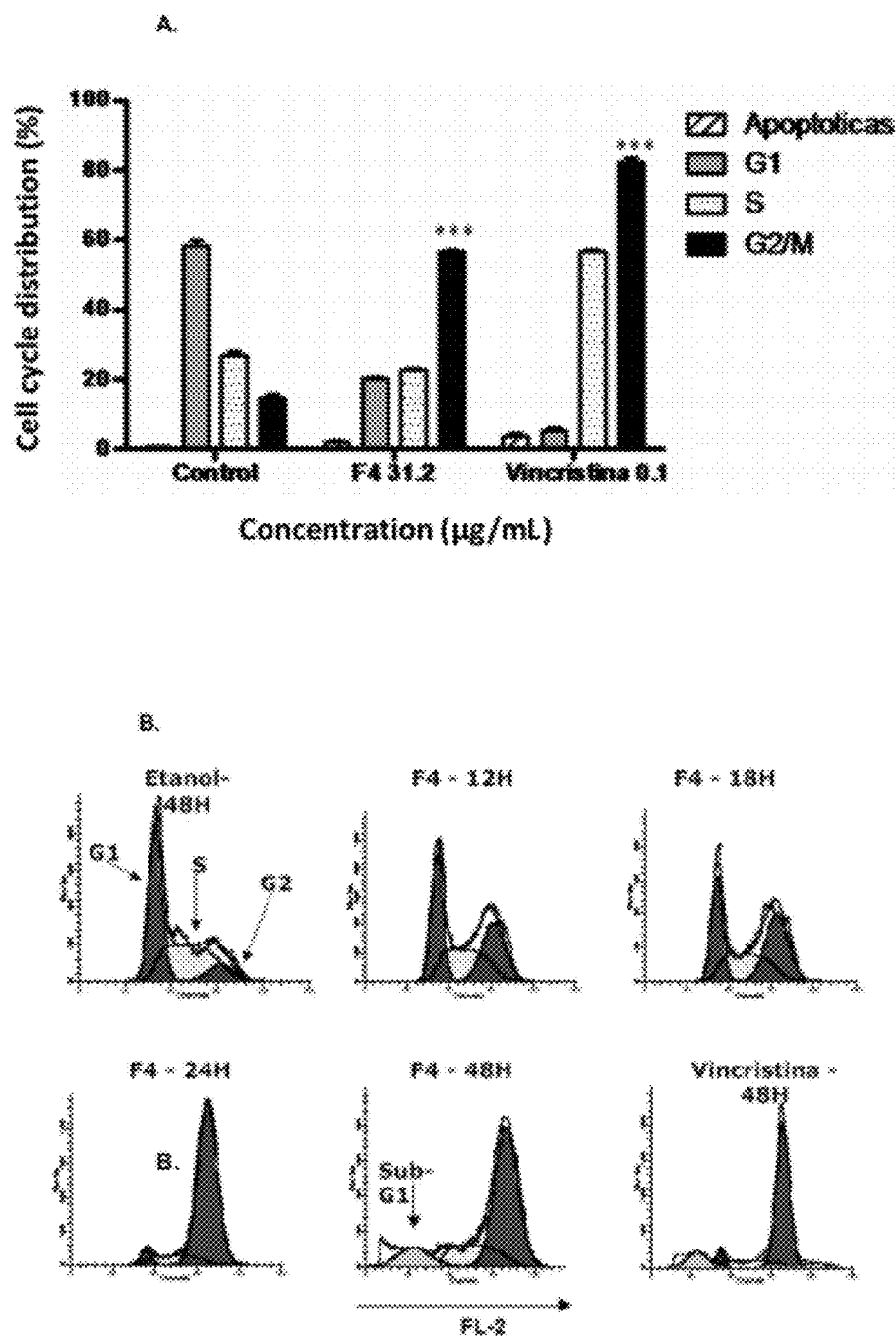
FIG. 5 shows a G2/M cell cycle arrest in tumor cell line A375 induced by treatment with F4 bioactive fraction of *Petiveria alliacea*. (A) Cell cycle distribution in ethanol (negative control), F4 bioactive fraction and vincristine (positive control) treatments. (B) Cell cycle distribution of tumour cell line A375 treated with F4 bioactive fraction at 12, 24 and 48 h.

FAST bioactive fraction induces a decrease in clonogenic capacity in 4T1 and K562 tumour cells lines (example 2, FIG. 2), additionally induce a glucose metabolism alteration by increasing in pyruvate kinase mRNA expression in 4T1 cell line measured by RT-PCR (example 3, FIG. 3). The fraction was characterized using HPLC-UV and mass spectroscopy (MS) (FIG. 4) in a liquid chromatography time-of-flight mass spectrometry (LC-TOF-MS) in both positive and negative ESI modes, allowing established the presence of this compounds by de-replication analysis:

| RT (min) | m/z ratio | Identified compounds |
|---|---|---|
| 29.37 | 314 | Petiveral/leridol |
| 33.42 | 298 | Leridal 7-demethyl |
| 48.27 | 278 | Dibenzyl trisulfide |

Relative abundance of marker compounds in FAST bioactive fraction of *Petiveria alliacea* were established from MS results like a characterization parameter of the same.

TABLE 2

| Compound | % weight respect total bioactive fraction |
|---|---|
| 4-ethyl petiveral | 0.01-31 |
| Lignoceric acid | 0.01-25 |
| Dibenzyl disulfide | 0.01-9 |
| Dibenzyl tetrasulfide | 0.01-9.5 |
| Dibenzyl trisulfide | 3.8-14 |
| Leridal 7-demethyl | 0.01-7 |
| Leridal Chalcone | 0.01-36 |
| Leridol | 0.01-15 |
| Myricitrine | 0.01-9 |
| Petiveral | 0.01-55 |
| Pinitol | 0.01-19 |
| S-benzyl cysteine sulfoxide | 0.01-5 |
| Senfol | 0.01-16 |

Preferably, FAST bioactive fraction of *Petiveria alliacea* contained the marker compounds according to table 3:

TABLE 3

| COMPOUND | % weight respect total bioactive fraction |
|---|---|
| 4-ethyl petiveral | 0.01-5 |
| Lignoceric acid | 0.01-5 |
| Dibenzyl disulfide | 0.01-5 |
| Dibenzyl tetrasulfide | 0.01-5 |
| Dibenzyl trisulfide | 3.8-7 |
| Leridal 7-demethyl | 3.8-7 |
| Leridal Chalcone | 0.01-5 |
| Leridol | 0.01-5 |
| Myricitrine | 0.01-5 |
| Petiveral | 20.6-38.2 |
| Pinitol | 0.01-5 |
| S-benzyl cysteine sulfoxide | 0.01-5 |
| Senfol | 0.01-5 |

Figure 9:
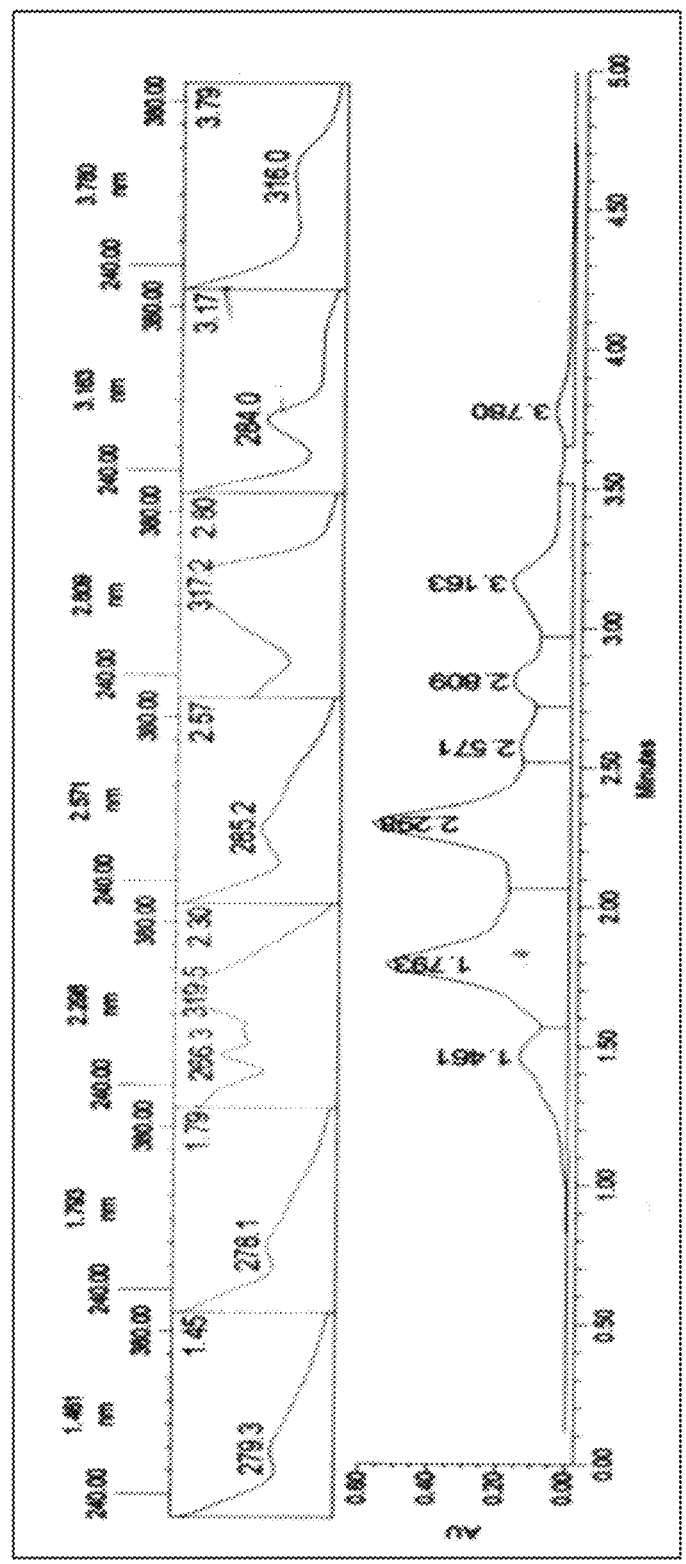
FIG. 9 shows the F4 bioactive fraction chromatogram obtained by HPLC (RP-18, mobile phase $H_2O$: ACN (4:6)) coupled to PDA detector.
Figure 10:
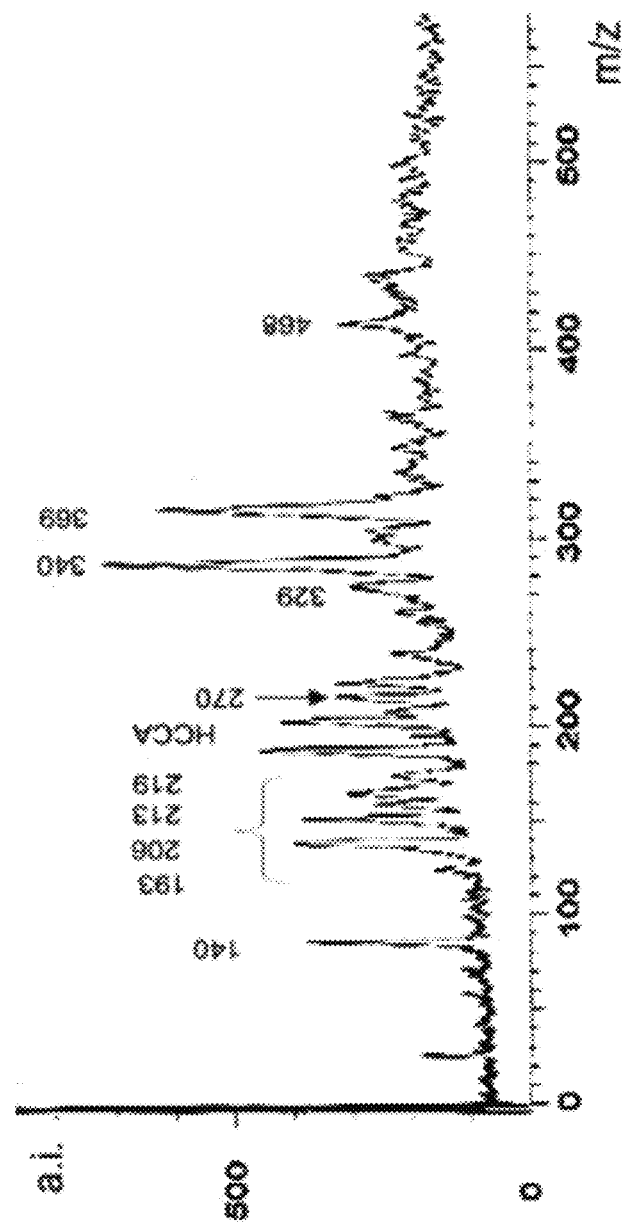
FIG. 10 shows the MS of F4 bioactive fraction of *Petiveria alliacea* obtained in a MALDI-TOF-MS with HCCA matrix.

F4 bioactive fraction presents multiple activities, inducing an increase in apoptotic population ($G_0/G$) with an increase of $G_2$ phase in different tumoural cell lines. Also, induce actin filaments reorganization in cytoskeleton and DNA fragmentation independent of mitochondrial pathway (examples 4 to 7, FIGS. 5 to 8). The fraction was characterized using HPLC-PDA (FIG. 9) and MS-MALDITOF (FIG. 10). F4 bioactive fraction shows seven (7) characteristically peaks in an analysis by HPLC coupled to PDA detector using RP-18 column and mobile phase H2O: ACN (4:6), its characteristic chromatographic fingerprint is shown in table 4:

| Peak | Retention time (min) | Area (%) | $\lambda$ (nm) |
|---|---|---|---|
| 1 | 1.46 | 8.5 | 279 |
| 2 | 1.79 | 30.8 | 278 |
| 3 | 2.29 | 30.0 | 266-319 |
| 4 | 2.57 | 6.0 | 285 |
| 5 | 2.80 | 7.5 | 317 |
| 6 | 3.16 | 12.2 | 284 |
| 7 | 3.78 | 5.0 | 316 |

To identify the compounds present in bioactive fraction of *Petiveria alliacea*, a MALDI-TOF-MS with HCCA matrix was performed and using de-replication analysis were established the presence of this compounds

| MW | Compound |
|---|---|
| 140 | Senfol |
| 193 | Pinitol |
| 206 | Leridal chalcone |
| 213 | Dibenzyl disulfide |
| 270 | Dibenzyl trisulfide |
| 340 | 4-ethyl petiveral |
| 369 | Lignoceric acid |
| 468 | Myricitrine |

Relative abundance of marker compounds in F4 bioactive fraction of *Petiveria alliacea* were established from MS results like a characterization parameter of the same.

TABLE 6

| COMPOUND | % weight respect bioactive fraction |
|---|---|
| 4-ethyl petiveral | 17-31 |
| Lignoceric acid | 13-25 |
| Dibenzyl disulfide | 4.5-9 |
| Dibenzyl tetrasulfide | 0.01-5 |
| Dibenzyl trisulfide | 8-14 |
| Leridal-7-demethyl | 0.01-5 |
| Leridal Chalcone | 9-16.5 |
| Leridol | 0.01-5 |
| Myricitrine | 4.5-9 |
| Petiveral | 0.01-5 |
| Pinitol | 10-19 |
| S-benzyl cysteine sulfoxide | 0.01-5 |
| Senfol | 9-16 |

Figure 13:
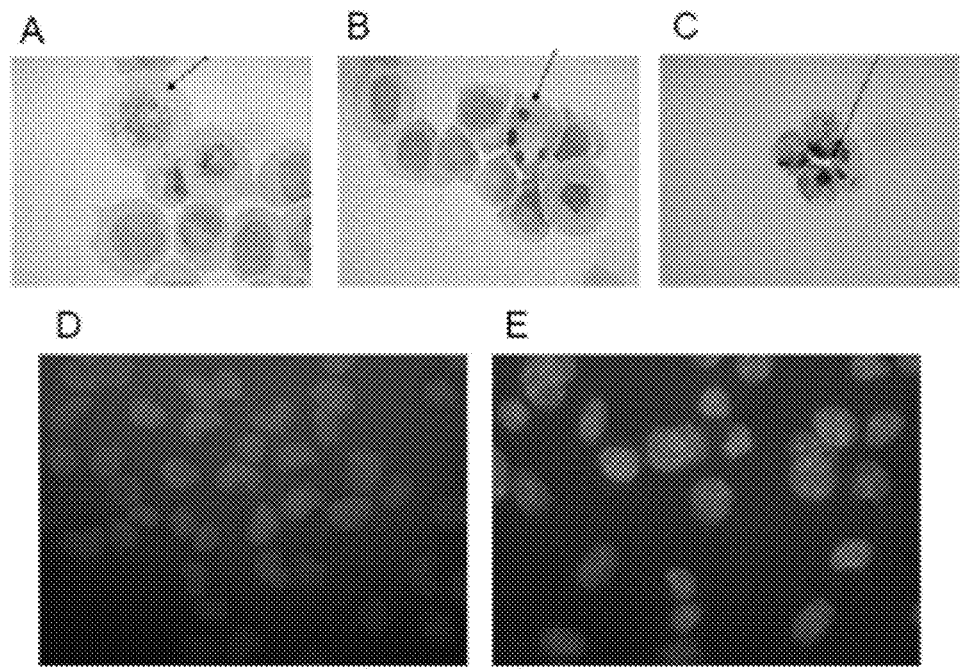
FIG. 13 shows chromatin condensation and nuclear fragmentation in tumour cell line NB4 treated with S3 bioactive fraction of *Petiveria alliacea* (31.2 μg/ml) during 24 h.
Figure 14:
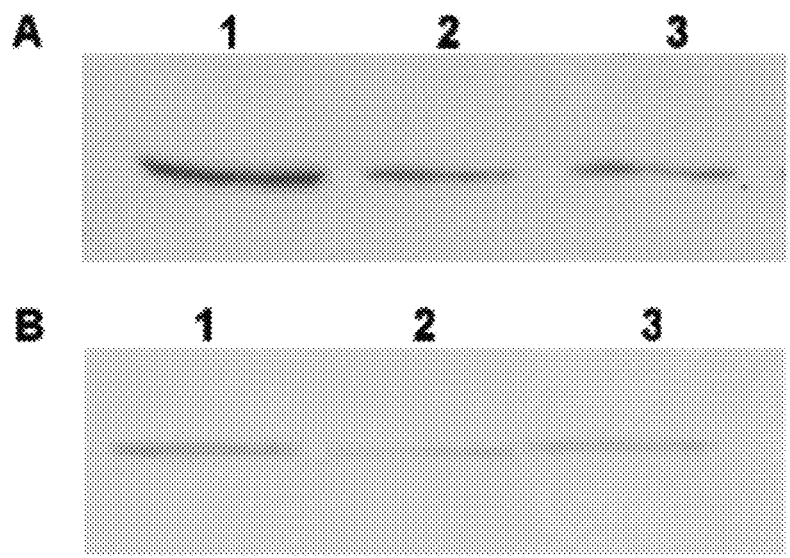
FIG. 14 presents decreased expression of Hsp70 in tumour cell line K562 by treatment with S3 bioactive fraction of *Petiveria alliacea* with (A) or without (B) thermal stress.
Figure 15:
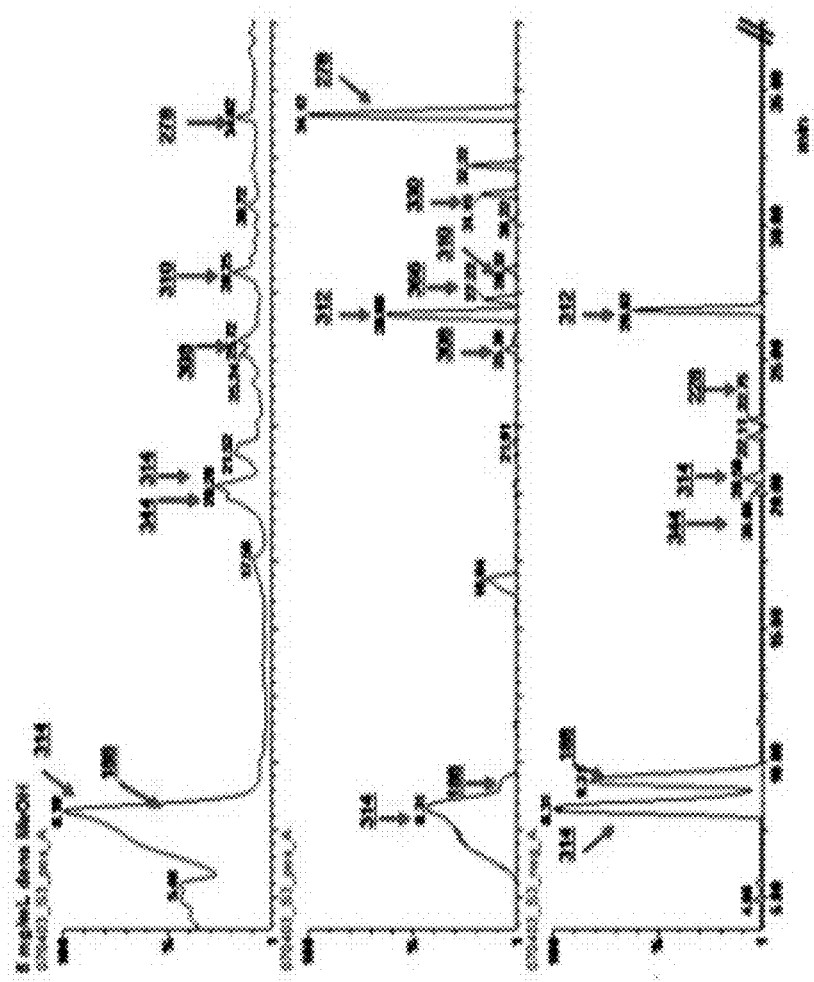
FIG. 15 shows the MS of S3 bioactive fraction of *Petiveria alliacea* obtained in a liquid chromatography time-of-flight mass spectrometry (LC-TOF-MS) in both positive and negative ESI modes.

S3 bioactive fraction decreases tumour cell viability in a dose-dependent manner inducing early nonreversible mitochondrial membrane depolarization (without affect cell cycle phases) in different human and murine tumour cell lines (example 8 to 11, FIGS. 11 to 13), additionally, induces a decrease in Hsp70 expression on tumoural cells with or without thermal stress (FIG. 14). Tumour cell death induce by S3 bioactive fraction associated to morphological changes and DNA fragmentation suggest that apoptosis is possibly mediated by endogen activation of endonucleases down-stream mitochondria. The fraction was characterized using mass spectroscopy (MS) in a liquid chromatography time-of-flight mass spectrometry (LC-TOF-MS) in both positive and negative ESI modes (FIG. 15) and HPLC-UV:

TABLE 7

| RT (min) | m/z ratio | Compounds identified |
|---|---|---|
| 22.58 | 228 | S-benzyl cysteine sulfoxide |
| 34.12 | 278 | Dibenzyl trisulfide |
| 28.32 | 310 | Dibenzyl tetrasulfide |
| 26.68 | 312 | Leridal Chalcone |
| 8.31 | 314 | Leridol |
| 20.38 | 314 | Petiveral |

Relative abundance of marker compounds in S3 bioactive fraction of *Petiveria alliacea* were established from MS results like a characterization parameter of the same.

| COMPOUND | % weight respect bioactive fraction |
|---|---|
| 4-ethyl petiveral | 0.01-5 |
| Lignoceric acid | 0.01-5 |
| Dibenzyl disulfide | 0.01-5 |
| Dibenzyl tetrasulfide | 5-9.5 |
| Dibenzyl trisulfide | 4.5-8.7 |
| Leridal-7-demethyl | 0.01-5 |
| Leridal chalcone | 19-36 |
| Leridol | 8-15 |
| Myricitrine | 0.01-5 |
| Petiveral | 32-55 |
| Pinitol | 0.01-5 |
| S-benzyl cysteine sulfoxide | 2-4 |
| Senfol | 0.01-5 |

In the scope of the invention the bioactive fractions of *Petiveria alliacea* could be formulated like pharmaceutical compositions including one or more pharmaceutically acceptable excipients. These pharmaceutical compositions could be designed to oral administration in solid or liquid pharmaceutical dosage forms, in heterodisperse systems to topical administration (i.e. W/O and O/W creams, gel, etc.) or to parenteral or rectal administration. These pharmaceutical compositions of the invention could be administrated to humans and other mammals orally, rectally, parenteral route, topically, intravaginally or like nasal spray.

Orally pharmaceutical compositions could include conventional pharmaceutical dosage forms, like tablets, capsules, buccal forms and oral liquids, suspensions or solutions. Capsules could contain active molecules mixed with excipients and diluents like but not restricted to: pharmaceutically acceptable starch (i.e. corn, potato, etc.), sugars, artificial sweeteners, cellulose in powder (CMC, MC, EC, HPMC), flours, gelatins and gums, among others.

Pharmaceutical compositions in tablets can be manufacture by conventional compression procedures, wet or dry granulation and could be use excipients like but not limited to: diluents or fillers, binders, disintegrants, lubricants, surface modifiers, coloring agents, suspension or stabilizer agents, like but not limited to magnesium stearate, stearic acid, talc, sodium lauryl sulfate, micro crystalline cellulose, carboxy methyl cellulose, polyvinylpyrrolidone, gelatin, alginic acid, acacia gum, xanthan gum, sodium citrate, silicates complex, calcium carbonate, lactose, kaolin, mannitol, sodium chloride, dry starch and sugar in pharmaceutical grade. Also, orally pharmaceutical compositions of the invention could be conventional release delivery or controlled and sustained release delivery to modify release of active agents.

In a further aspect, the invention presents a pharmaceutical combination for treating cancer, comprising a bioactive fraction of *Petiveria alliacea* or the pharmaceutical composition that containing the same and at least one immunostimulant that can produce the phenotypic and/or functional maturation of the dendritic cells.

In the scope of the invention the immunostimulant agents that can produce the phenotypic and/or functional maturation of the dendritic cells are fractions or isolated compounds from mushrooms or plants, examples preferred are polysaccharides and/or glycopeptides obtained from: *Ganoderma lucidum*, *Astragalus membranaceus*, *Grifola frondosa*, *Phellinus linteus*, *Cordyceps militaris*, *Lentinus edodes*, *Coriolus versicolor*, *Agaricus blazei* or *Petiveria alliacea*.

*Ganoderma lucidum* is a mushroom widely used in China, Korea and Japan with a history in traditional medicine for more than four millennia. In Japan is named Reishi or Mannetake, in China and Korea Ling Chu, Ling Chih and Ling Zhi (immortality mushroom).

Presence of steroids, lactones, alkaloids, polysaccharides and triterpenes has been identified in the mushroom and mycelium. *G. lucidum* has shown immunomodulatory, antiviral and antitumor activities. As active metabolites are a branched glycopeptide (PS-G) (1→6)-β-D-glucane (95%) and a peptide (5%), having antineoplasic activity (Wang et al., 1997). The peptide also increases NK cells cytotoxic activity and the secretion of TNF-α and IFN-γ in macrophages and lymphocytes respectively (Lee et al., 1995). Moreover, it has been shown that PS-G induces DC changes in phenotype and function (Lin et al., 2005).

*Astragalus membranaceus* (Bunge) is a Chinese plant widely known for its immunomodulatory activity. Various polysaccharides have been isolated from its root as Astragalan I, which is a neutral hetero polysaccharide (36 KD) containing glucose, galactose and arabinose; astragalan II and III having β-glucans of 12 and 34 kD, respectively; AMemP a polysaccharide (60 kD) of acidic nature with high content of uronic acid, Amons an acid polysaccharide (76 KD) comprising arabinose, galactose, galacturonic acid and glucuronic acid in relation 18:18:1:1 (Shimizu et al., 1991) and APSID-3 a heteropolysaccharide containing arabinose, rhamnose and methylgalacturonate (Wang et al., 2006). The polysaccharides fractions can induce DC morphological maturation in vitro increasing surface CD-11c and MHC class II expression, and reducing the phagocytic capacity (uptake of FITC-dextran) (Shao, et al., 2006).

*Grifola frondosa* known as Maitake is an edible mushroom with a pleasant flavor and aroma, being a constituent of a wide variety of traditional Chinese medicines. From *G frondosa* derives a polysaccharide called fraction D, used as nutritional supplement in cancer treatment. The fraction is obtained from the mycelium or fruit by extraction with hot water, ethanol precipitation and subsequently treatment with acetic acid and alkali. It comprises β-1,6-glucans with β-1,3 branches (grifolan, sonifilan and SSG) and a protein of 1000 KD. In normal mice C3H/HeJ, fraction D has shown to increase innate and adaptive immune responses, suggesting that the fraction induces a dominant Th2 response by activating macrophages and increasing IL4 and IL10 secretion, complementary to the activation of antigen presenting cells (CD69 and CD89 increased expression) after 4 hours of treatment (Kodama, Muraya & Nanba, 2004).

*Phellinus linteus* is a perennial basidiomycete native to China and Korea from which a protein-polysaccharide complex (PPC) have been isolated. The polysaccharide within the complex is acidic with immunostimulatory properties. The PPC has a weight of 73 KD, 73% corresponding to the polysaccharide (composed mainly of glucose and mannose) and 13% to the protein (Asp, Thr, Ser, Glu, Pro, Gly, Ala, Val). PPC induces an increase dose-dependent in expression of co-stimulatory molecules CD86 and MHC class II and phenotypic maturation of myeloid DC by decreasing the endocytic cell capability after treatment of 24 h (Kim, et al., 2006). Equally, acidic polysaccharides have shown to be stimulators of lymphocytes T proliferation, tumor growth inhibitors and phenotypic maturation inducers of murine bone marrow derived DC increasing the expression of CD80, CD86, MHC I, MHC II and IL12 and reducing the dextran uptake (Park S K, et al. 2003).

*Cordyceps militaris* is a parasitic Lepidoptera larvae fungus used for centuries in traditional Chinese medicine for its antitumor and hypoglycemic properties. Within the isolated mycelium bioactive compounds are nucleosides (cordycepin, opicordina) galactomannan, tryptophan and polysaccharides (Li et al. 2006). C. militaris aqueous fraction has a polysaccharide-rich fraction exhibiting antitumor and immunomodulatory activities in vivo and in vitro. The fraction induces phenotypic and functional maturation of murine myeloid DC, increasing the expression of CD40, CD54, CD80, CD86, MHC II and secretion of IL-12. Similarly, DC fraction treated and pulsed with tumor lysate P815 promotes cytotoxicity to cytotoxic T lymphocytes (Gi-Young, et al. 2006).

*Lentinus edodes* is a mushroom used in traditional medicine as well as a nutrient. In Japan is known as "shiitake" and in China as Gu Xiang. Several studies in animals and humans have demonstrated its antitumor and immunostimulant activities. At least five polysaccharides have been isolated from *L. edodes* active fractions; lentinan—a high molecular weight polysaccharide (450 KD) commercially available in U.S. and Europe, corresponding to a branched β-1,3-glucan with two units of β-1,6-D-glucopyranosyl per five β-1,3 linear glucopyranoside units, is water soluble and present at very low concentrations (0.02%) in fresh mushrooms (Sasaki and Takasuka, 1976). LEM is a heteropolysaccharide protein coupled derivative from the mycelium and KS-2- is a β-mannan peptide containing amino acids as serine, threonine, alanine and proline. *L. edodes* aqueous extracts have shown cytostatic activity in vitro on MCF-7 cells (human breast adenocarcinoma) tested by MTT cytotoxicity assay and as immunomodulator in terms of mitogenic and co-mitogenic activity by lymphocyte transformation test (LTT). LTT is an assay based on the proliferation increased of rat thymocytes by lymphocytes T mitogens in vitro (Israilides, et al., 2008).

*Coriolus versicolor* is a basidiomycete mushroom used in traditional Chinese medicine having immunostimulant and antitumor properties. Extracts from *C. versicolor* are commercially used in Japan and other countries as anticancer drugs (PSK) or dietary supplements (PSP and VPS). PSK is a polysaccharide protein bound mainly composed of β-1,4-glucan, isolated from CM-101 strain that induces an increase in cytokines secretion on peripheral blood human mononuclear cells in vitro, and increases TNF-α and IL-8 expression on healthy volunteers and gastric cancer patients. Also, PSK promotes phenotypic and functional DC (mononuclear cells derived, CD14+ and cultured with PSK) maturation, increases HLA class II, CD80, CD86 and CD83 expression, decreases FITC-dextran uptake, increases IL-12 secretion, the mixed lymphocyte allogeneic reaction and induces antigen specific cytotoxicity (Kanazawa, et al., 2004). PSP a polysaccharide-peptide isolated from strain VOC-1 corresponding to a heteropolysaccharide containing an α-1,4-glucan, a β-1,3-glucan, rhamnose and arabinose, with a molecular weight of 100 kD. PSP has shown antitumor activity in patients with esophageal, gastric and lung cancer. Also induces IL-2 and IFN-γ secretion and in animal models lymphocyte T proliferation (TB Ng, 1998).

*Agaricus blazei* Murril is a native Brazilian mushroom known as "Cogumelo do Sol" in Brazil or "Himematsutake" in Japan. The mushroom is traditionally used in atherosclerosis, hepatitis, hyperlipidemia, diabetes, dermatitis and cancer treatments (Firenzouli, et al., 2007). Within its active metabolite is the water soluble proteoglycan with 45% of protein content and a 50% of an β-1,6-glucan (branch with β-1,3), which induces B cells polyclonal activation and exerts as a potent inhibitor of tumor growth and metastasis. It also increases the expression of co-stimulatory molecules (CD80 and CD86) and MHC class II, decreases the FITC-dextran uptake and increases the allogeneic proliferation of lymphocytes T by murine DC bone marrow derived after their treatment with the proteoglycan during 24 h (Kim, et al., 2005).

In a further object, the invention presents the use of the bioactive fraction of *Petiveria alliacea* like drug substance to manufacture drug products for treating cancer. Additionally, the invention shows the use of the bioactive fraction of *Petiveria alliacea* with other isolated compounds, fractions or extracts to manufacture drug products. Also, is considered part of the invention the use of the bioactive fraction of *Petiveria alliacea* or the pharmaceutical composition that containing the same as adjuvant agent in a chemotherapy regime for treating cancer.

In a further object, the invention includes a kit for treating cancer comprising a first pharmaceutical composition containing the bioactive fraction of *Petiveria alliacea*, a second pharmaceutical composition containing one or more immunostimulant agents that can produce the phenotypic and/or functional maturation of the dendritic cells and at least one or more pharmaceutically acceptable excipients and optionally instructions for use In another object, the invention presents a method for treating cancer comprising sequential administration of at least a bioactive fraction of *Petiveria alliacea* or the pharmaceutical composition that containing the same and, in a time between 24 hours and 2 weeks, the administration of at least one immunostimulant agent or pharmaceutical composition that containing the same that can produce the phenotypic and/or functional maturation of the dendritic cells.

Optionally, the method for treating cancer comprise simultaneous or sequential administration of at least a bioactive fraction of *Petiveria alliacea* or the pharmaceutical composition that containing the same and a chemotherapeutic drug use in chemotherapy regime.

Fraction and immunostimulant agents dose levels in the pharmaceutical combination of the invention could vary to obtain the drug substance required to get the therapeutic response depending on physiological and pathological individually conditions, composition, and administration way. Dose level selected depend upon fraction potency, administration way, disease severity and medical history of each patient.

Fraction and compounds total daily dose used in pharmaceutical compositions could vary in a range since 0.001 to 1000 mg/Kg/day. To oral administration way, the preferred doses are in the range since 0.001 to 5 mg/Kg/day. The effective daily dose could divide in multiple doses consequently the invention comprise multiple doses pharmaceutical compositions that contain the effective amount or multiple doses that allowed effective daily dose after several administrations.

The examples presented herein are just illustrative of scientific facts, that support the invention and should not be understood as invention limits.

Cell Lines

Mel-Rel was established as a melanoma cell line from tumors developed in REL transgenic mice (gift from Dr. Armell Prevost, Cohin Hospital, Paris, France). A375 are human melanoma cells, courtesy of the Instituto de Investigaciones de la Universidad del Rosario (Bogotá, Colombia). NB4 (human myeloid leukemia), 4T1 (murine mammary adenocarcinoma) and K562 (human erythroleukemia) cell lines from ATCC. Cells were placed in RPMI-1640 supplemented medium (10% FBS, 2 mM L-glutamine, 100 U/ml penicillin, 100 µg/ml streptomycin, 0.01 M Hepes) and incubated under humidified environment at 37° C. and 5% $CO_2$. Adherent cells at 80% of confluence were detached (trypsin/EDTA), washed (PBS) and suspended in complete medium. Cytotoxicity evaluation was performed in 96 plates and fractions were diluted in ethanol or DMSO at levels below 0.2% (final concentration).

For assays in normal cells, human peripheral blood mononuclear cells (PBMC) from healthy volunteers were separated by density gradient centrifugation (Ficoll-Hypaque, Amersham, Biosciences). PBMC were suspended in RPMI-1640 supplemented medium (10% FBS, 2 mM L-glutamine, 100 U/ml penicillin, 100 µg/ml streptomycin, 0.01 M Hepes) and incubated under humidified environment at 37° C. and 5% $CO_2$.

Example 1

Tumour Cell Death Induced by *Petiveria Alliacea* Crude Extracts

NB4 cells were treated with crude extracts of *Petiveria alliacea* (250 µg/mL) over 24 h, and cell viability was calculated with trypan blue. Etoposide (100 µg/mL) was used as positive control. Results are expressed like viability percent (FIG. 1). Plot shows clearly that ethanol crude extract (used in state of the art) induce just a mortality of 50% in tumour cells while ethyl acetate extract (basis of present invention) induce a 80% mortality, showing higher biological activity in the extract of the invention compared to extracts conventionally used.

Since these results, ethyl acetate crude extract were selected as matrix to obtain fractions that will be describes below and that claimed in the present invention.

Example 2

Effect of Fast Bioactive Fraction of *Petiveria Alliacea* on 4T1 Cell Line Clonogenic Capacity 4T1 cells ($2.5 \times 10^5$ cells/well) plated (24-well plate) were treated with FAST 7:3 fraction at 40 and 20 µg/ml, vincristine 100 mM (conventional chemotherapeutic drug) as positive control or 0.2% ethanol and incubated for 6 h under humidified environment at 37° C. and 5% $CO_2$. After treatment cells were re-plated onto 0.5% agar dishes (60-mm, 20,000 cells/dish), incubated for 14 days (37° C. and 5% $CO_2$) and stained with violet crystal (0.4% in ethanol). Cell colonies with more than 50 cells were counted. Treatments were performed in triplicate, and results expressed as mean±SEM (FIG. 2).

FAST bioactive fraction induces a decrease statistically significant in colonies number in 4T1 tumour cell line at concentrations of 40 and 20 µg/ml, showing the activity of *P. alliacea* fraction such as inhibitor of clonogenic capacity in tumour cell lines.

Example 3

Pyruvate Kinase Isoform PK-LR Gene Expression in 4T1 Cell Line Treated with Fast Bioactive Fraction 4T1 cells were treated with FAST 7:3 fraction at 20 µg/ml or ethanol (negative control) for 6, 12, 16 and 24 h. RNA was extracted using TRIzol and cDNA synthesis was performed using superscript III. LightCycler FastStart DNA Master Plus SYBR Green I was used to pyruvate kinase gen amplification by RT-PCR.

It was observed a pyruvate kinase mRNA increase over 20 folds in 4T1 cell line treated with FAST bioactive fraction of *Petiveria alliacea*. This result confirms the alteration in glucose metabolism induced by P. alliance fraction that explains antitumoral activity reported to *Petiveria alliacea* fraction (FIG. 3).

Example 4

G2/M Cell Cycle Arrest in Tumor Cell Line A375 Induced by Treatment with F4 Bioactive Fraction of *Petiveria Alliacea*

Cytotoxic activity of F4 bioactive fraction was evaluated in in tumor cell line A375 at concentrations since 3.9 until 125 µg/mL. Evaluations were performed when over 50% population were death or showed morphologic alterations. After treatment for 24 h, it was observed fraction's cytotoxicity and morphologic alterations (changes in shape, detachment) at 31.2 µg/mL.

From these results cell cycle effect was evaluated, tumor cells lines starved for 72 h (to induce arrest in G1 phase), seeded in 12-well plate ($4 \times 10^5$ cells/well) were treated with F4 fraction (31.2 µg/mL) at 12, 18, 24 and 48 h under humidified environment at 37° C. and 5% $CO_2$. After treatment, cells were washed and fixed with ethanol (ice-cold 70%) during 18 h. After fixing, cells were suspended in PBS 1×, 100 U/ml RNase, 50 µg/ml of propidium iodide (Sigma, St. Louis, Mo.) and incubated at room temperature for 30 min. Cell DNA content was measured by flow cytometry using a FACScalibur, (Becton Dickinson, Fullerton, Calif. For cytometric data 50,000 cellular events were collected per sample and analyzed with Cell Quest software (Becton Dickinson). Cell cycle distribution percentages are calculated by Modfit LT software. FACScalibur calibration is performed with the DNA QC Particle Kit (Becton Dickinson).

FIG. 5A shows clearly G2/M cell cycle arrest in tumour cells induce by F4 bioactive fraction like vincristine used as positive control. FIG. 5B shows F4 effect (31.2 µg/mL) over A375 cell cycle. Plot shows G2 phase accumulation (60%) for cells treated with fraction F4 compared to 18% in no treatment cells. Vincristine induce a G2/M cell cycle arrest closely to 80%.

Example 5

Cytoskeleton Alterations in A375 Treated With F4 Fraction

A375 and Mel-Rel cells ($5 \times 10^4$ cells/ml) plated on glass coverslides (13 mm diameter), precoated with collagen (Sigma, St. Louis, Mo.) were allowed to adhere for 16 h.

Afterwards, treated with F4 fraction for 24 h and incubated under humidified environment, at 37° C. and 5% $CO_2$. Treated cells were washed (PBS) and fixed (2% paraformaldehyde in PBS) for 30 min at 4° C. Fixed cells were wash twice with 1% PBS-BSA, incubated with cold acetone for 1 min, washed (1% PBS-BSA) and incubated with phalloidin conjugated to Oregon-green (Molecular Probes, Eugene, Oreg., USA), diluted in 1% PBS-BSA (1/40) for 30 min. Slides were mounted with prolong antifade kit (Molecular Probes, Eugene, Oreg., USA) and analyzed under fluorescence microscope (Olympus, Japan).

Figure 6:
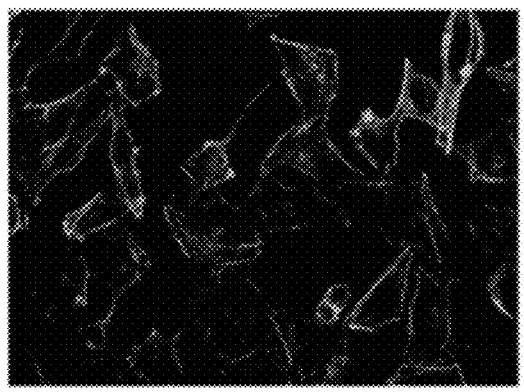
FIG. 6 shows actin filaments organization in tumor cell line A375 (A) and treated with F4 bioactive fraction of *Petiveria alliacea*.
Figure 6:
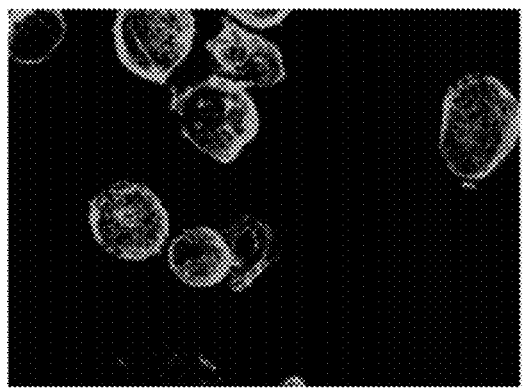

FIG. 6 in panel B shows F4 bioactive fraction effect on actin filaments architecture and organization. Cells treated with F4 fraction don't spread and filamentous structures were observed disassembled or reorganized and accumulated in sub-membranous areas. Actin filaments were observed like granules mainly located in cell periphery. Control cells (panel A) showed cytoskeleton architecture organization.

Example 6

Dna Fragmentation in Tumor Cell Line A375 Induced by Treatment with F4 Bioactive Fraction of *Petiveria Alliacea*

A375 and Mel-Rel cells ($5 \times 10^4$ cells/ml) plated on glass coverslides (13 mm diameter), precoated with collagen (Sigma, St. Louis, Mo.) were allowed to adhere for 16 h. Afterwards, treated with F4 fraction (31.2 µg/mL) for 24 h and incubated under humidified environment, at 37° C. and 5% $CO_2$. Treated cells were washed (PBS) and fixed (2% paraformaldehyde in PBS) for 30 min at 4° C. Fixed cells were wash twice with 1% PBS-BSA, incubated with cold acetone for 1 min, washed (1% PBS-BSA) and incubated with 300 nM of DAPI (Sigma, St. Louis, Mo.) for 5 min. Slides were mounted with prolong anti-fade kit (Molecular Probes, Eugene, Oreg., USA) and cells analyzed under fluorescence microscope (Olympus, Japan).

Figure 7:
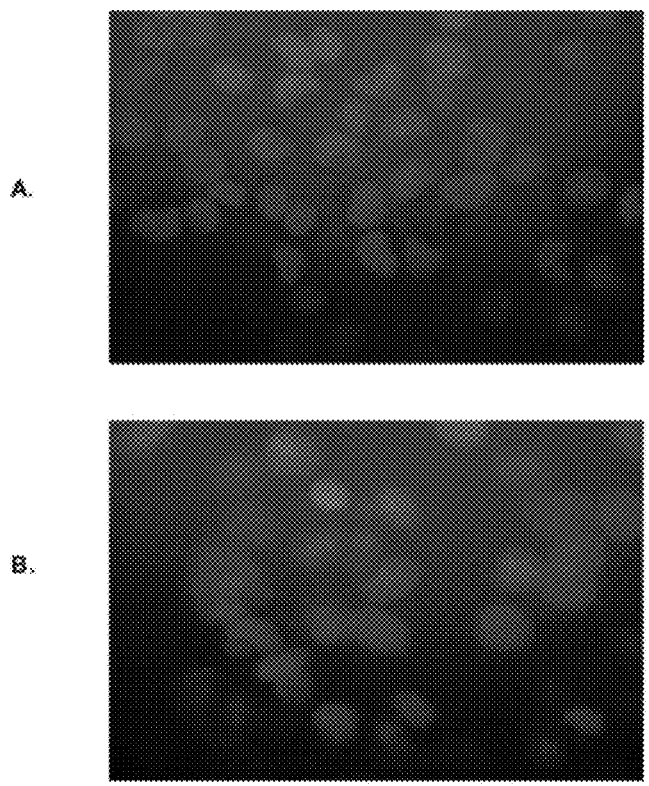
FIG. 7 shows DNA fragmentation in tumor cell line A375 induced by treatment with F4 bioactive fraction of *Petiveria alliacea* (B) compare to control (A).

FIG. 7 (panel B) shows the F4 fraction effect over DNA fragmentation induced possibly by endogen activation of endonucleases in a mitochondrial independent way.

Example 7

F4 Bioactive Fraction Effect over Growth of Human Mononuclear Cells

Human PBMC were seeded ($2 \times 10^5$ cells/well) on 96-well plates and incubated with or without phytohemagglutinin (PHA, GibcoBRL) for 12 h. Afterwards, PBMC were treated with F4 fraction (250 to 1.9 µg/ml), or vincristine for 30 h. After treatment cells were centrifuged, F4 fraction removed and lastly cells were carefully washed 3 times (PBS) before adding the MTT. Next 12 µl of MTT 12 mM [3-(4,5-dimethylthiazol-2-yl)-2,5-diphenyl tetrazolium bromide] (Molecular Probes, Eugene, Oreg., USA) in PBS was added to each well and incubated for 4 h at 37° C. Formazan crystals were dissolved with SDS-HCl 0.01M. MTT results were read at 540 nm in a Multiskan MCC/340 (LabSystems).

Figure 8:
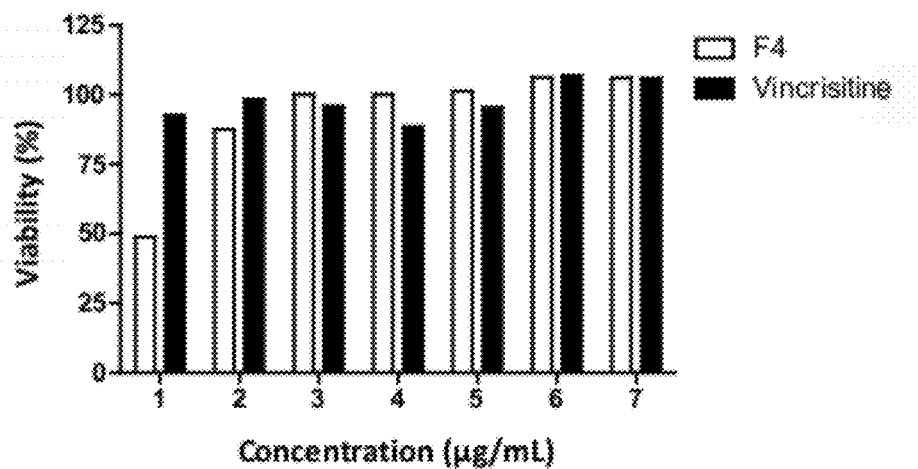
FIG. 8 presents F4 bioactive fraction of *Petiveria alliacea* effect over growth of human mononuclear cells with (B) or without (A) phytohemaglutinin.
Figure 8:
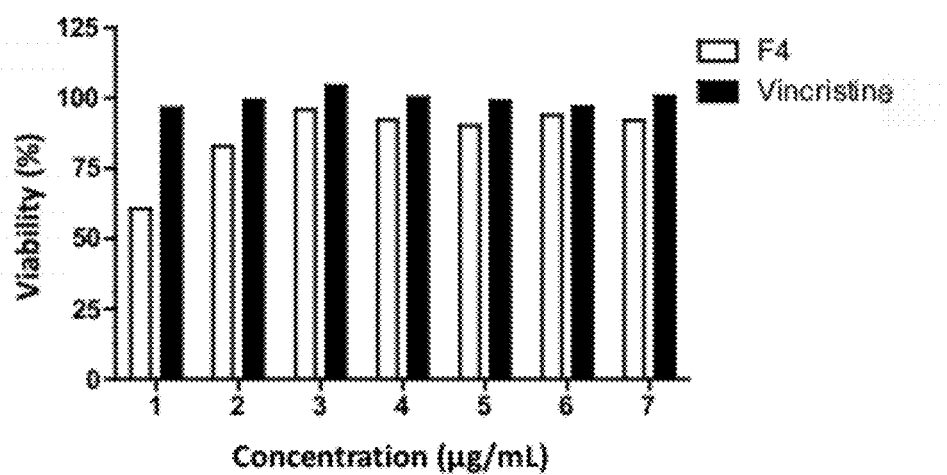

FIG. 8 presents F4 bioactive fraction effect over growth of human mononuclear cells with (B) or without (A) phytehmaglutinin. Plot clearly shows that F4 fraction has no effect over normal mononuclear cells like vincristine. The lack of effect of vincristine is explained by its specific activity in high rate replication cell cytoskeleton, such as tumoural cells. It means that F4 fraction and vincristine showed a high specificity over tumoural cells.

Example 8

Figure 11:
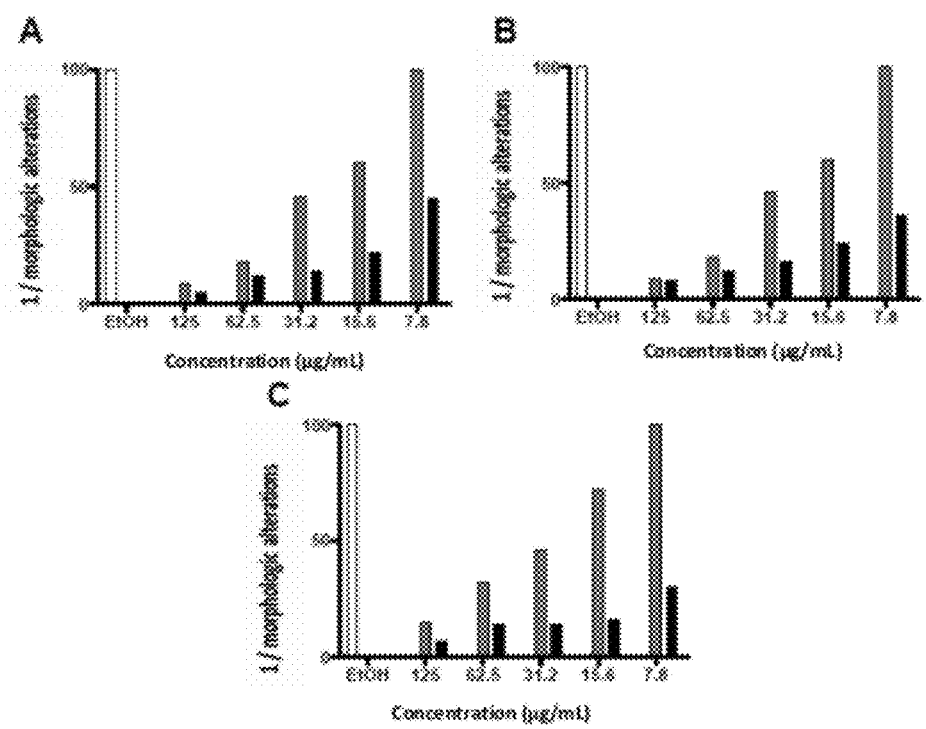
FIG. 11 presents S3 bioactive fraction of *Petiveria alliacea* effects over NB4 (A), Mel-Rel (B) and K562 (C) morphology and viability.

S3 Bioactive Fraction Effects over Nb4 (A), Mel-Rel (B) And K562 (C) Morphology and Viability NB4 (A), Mel-Rel (B) and K562 (C) cells plated (96-well plate) were treated with S3 fraction (125 to 7.8 µg/mL) and observed in an inverted microscopy to established morphological changes (intracellular vesicles) and viability cell test (trypan blue dye exclusion). S3 bioactive fraction induces morphological changes in all tumour cell lines suggesting cell death via apoptosis and/or necrosis according to apoptotic bodies presence and exploded cells (FIG. 11). Plot shows that S3 fraction (gray bars) compared to positive control—etoposide—(black bars) and negative control (ethanol). IC50 value (50% inhibition of cellular growth) was 45 µg/ml to different cell lines (calculated using Minitab 14 Probit analysis (MINITAB® Release 14.1. Minitab Inc. 2003 Statistical Software).

Example 9

Mitochondrial Membrane Alterations Induced by Treatment with S3 Fraction over Tumour Cell Lines NB4, Mel-Rel and K562

Figure 12:
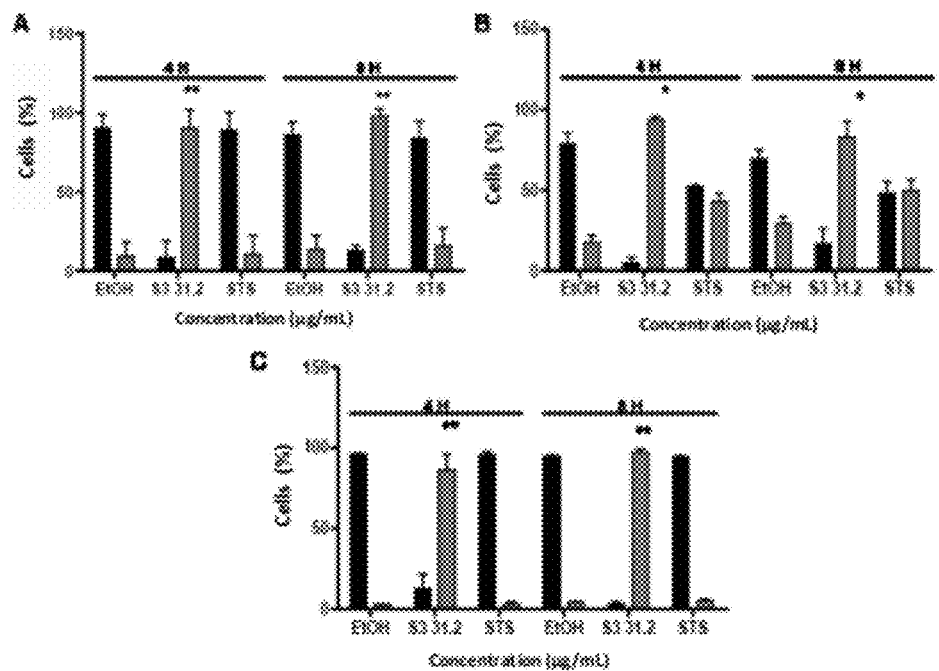
FIG. 12 presents mitochondrial membrane effect of S3 bioactive fraction of *Petiveria alliacea* over tumour cell lines NB4, Mel-Rel and K562.

Mitochondria membrane potential (MMP) was measured by flow cytometry, using JC-1, a lipophilic cationic probe (5,5',6,6'-tetrachloro-1,1',3,3'-tetraethyl-benzimidazolcarbocyanine iodide), (Sigma, St. Louis, Mo.). JC-1 (10 µg/ml in PBS) is added to $3 \times 10^5$ cells/ml and incubated for 10 min at 37° C. Data analysis was processed by Cell Quest software (Becton Dickinson). All treatments were performed in triplicate, and results expressed as mean±SEM. FIG. 12 shows mitochondrial membrane depolarization induced by S3 treatment (31.2 µg/mL) compared to negative control (EtOH) over NB4, Mel-Rel and K562 cell lines. Mitochondrial membrane depolarization induced by S3 treatment on tumour cell lines is maintained over time (until 8 h) suggesting programmed cell death through mitochondrial pathway. Additional assays allow established that effect on mitochondrial membrane is obtain at concentration of 15.6 µg/mL.

Example 10

Chromatin Condensation and Nuclear Fragmentation in Tumour Cell Line NB4 Treated with S3 Bioactive Fraction Hematoxylin-eosine and DAPI (4',6-diamidino-2-phenylindole, Sigma) stained cells were monitored under microscope to evaluated the type of cell death induced by the S3 fraction. In brief, cells treated with S3 fraction for 24 h at 37° C. under humidified atmosphere and 5% CO2, were plated onto microscope slides by cytocentrifugation (Vybra cytospin, Japan) for 5 min at 500 rpm, fixed with ethanol and stained with hematoxylin (2 min) and eosin (45 seconds). Excess dye was removed with ethanol (3 washes) and microscope slides were monitored and photographed under a light microscope (Olympus CH30, Japan) at a magnification of 100×. For DAPI staining, cells plated on glass cover slides (13 mm/-E) previously collagen-precoated (6-10 µg/cm2) at a density of $5 \times 10^4$ cells for 16 h, were treated with S3 fraction at 37° C. under humidified atmosphere and 5% CO2 for 24 h. Subsequently, cells were washed (PBS) and fixed with paraformaldehyde (2% in PBS) for 30 min at 4° C. After washing twice with PBS-BSA (1%), cells were incubated in cold acetone (1 min); washed (1% PBS-BSA) and incubated for 5 min with DAPI 300 nM (Sigma, St. Louis, Mo.). Slides with prolong antifade kit (Molecular Probes) were observed under a fluorescence microscope (Olympus, Japan).

NB4 cells were trated with S3 fraction (31.2 µg/mL) and staurosporine as positive control, FIG. 13 shows tumour cells treated with negative control (EtOH) in active mitosis without interference of cell cycle (A), cells treated with S3 fraction (B) and staurosporine (C) showed nuclear fragmentation and DNA fragmentation, features of apoptosis cell death.

DAPI staining showed similar results, FIG. 13-D presents normal nuclei (vehicle) and 13-E fragmented nuclei after endonucleases activation in cells treated with S3 fraction (31.2 µg/mL). Nuclei fragmentation was confirmed by DNA fragmentation assay showing a coordinate DNA breakdown.

Example 11

Expression of HSP70 in Tumour Cell Line K562 by Treatment with S3 Bioactive Fraction K562 cells incubated on 6-well plates (2×106 cells/well) in 3 ml of supplemented medium were treated with S3 fraction (6.2 µg/ml) or quercetin and rutin (100 µM, positive control). Treated cells were divided into two groups: one group was incubated at 37° C. for 10 h, subjected to heat shock (42° C., 60 min) in a serological water bath, and then allowed to recover for 4 h at 37° C.; the other group was incubated for 15 h at 37° C. During the entire procedure, both groups were maintained with treatments After treatment, cells were lysed using TDLB buffer (1 M Tris-HCl pH 8, 5 M NaCl, 20% sodium azide, 10% SDS, 10% NP40, 10% sodium desoxicolate, 1% PMSF) for 30 min at 4° C. Proteins were quantified by Bradford assay (BIORAD), separated by electrophoresis (10% polyacrilamide gel) and transferred onto PVDF membranes. Protein identification was accomplished using a monoclonal primary antibody anti-Hsp70 (Hsp70 clone 283-48, kindly provided by Dr. Peter Van Endert INSERM Unit 580 Necker Hospital, Paris, France). For protein detection a super signal West Dura Extended Duration Substrate chemiluminescence kit (Pierce Lab) was used.

FIG. 14 shows a decrease in chaperone protein Hsp70 expression on K562 tumoural cells with (panel A) or without thermal stress (panel B), in a pattern similar to quercetin, a flavonoid well known by its effect on Hsp70 expression. Since S3 fraction decreases Hsp70 expression with or without thermal stress it could be assumed that fraction acting over heat sock factor-1 (HSF-1) or over its promoter, mechanism previously reported to quercetin Hsp70 regulation.

In examples 12 and 13 related to compounds or fractions capacity to induce phenotypic and/or functional maturation of the antigen presenting cells, dendritic cells were obtained according to this protocol.

Peripheral blood mononuclear cells (PBMCs) were obtained from fresh buffy coats (60 ml) of healthy volunteers. Mononuclear cells purification was carryout by Ficoll density gradient centrifugation (Amersham, GE Health Care Europe GmbH). Monocytes were isolated by positive selection using anti-CD14+ micro-beads with MiniMACS Systems according to manufacturer instructions (MiltenyiBiotec, BergischGladbach, Germany). The cells used in the assays had more than 98% of purity in accordance to flow cytometry estimations. Monocytes were cultured for 5 days in RPMI 1640 medium, 10% fetal calf serum (FCS), 2 mM glutamine, 100 IU/ml penicillin, streptomycin (Eurobio, Paris, France), granulocyte-macrophage colony-stimulating factor (GM-CSF) (800 IU/ml) and IL-4 (1000 IU/ml) (R&D Systems, Minneapolis, Minn., USA). On day 3 half of the medium was replaced with fresh media containing GM-CSF and IL-4. On day 5 the MDDCs were treated with LPS (1 µg/mL) as positive control and cells without maturation stimuli were used as negative control.

Example 12

Figure 16:
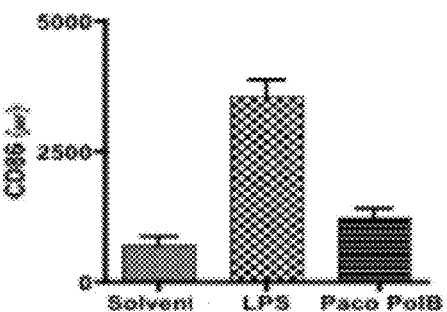
FIG. 16 presents CD86 and HLA-DR expression in a DC population treated with water (negative control), LPS (positive control) and the immunostimulant polysaccharide.
Figure 16:
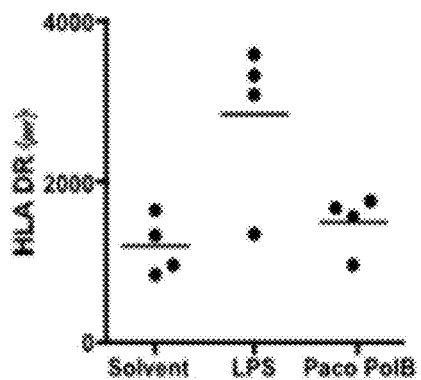
Figure 17:
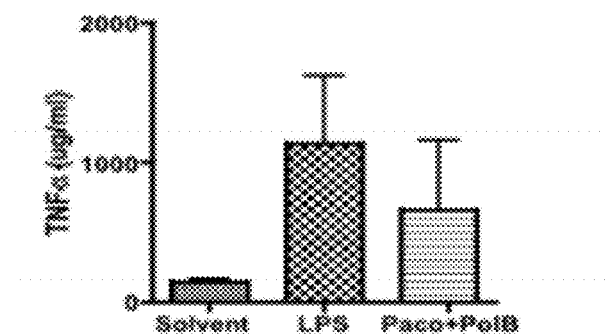
FIG. 17 shows TNF-α production measured by ELISA in a DC population stimulated with polysaccharide.

Costimulatory Molecules Expression over a Dc Population Treated with Polysaccharides Obtained from P. Alliacea MDDC were stimulated for 48 h with solvent, lipopolysaccharide (LPS) and a polysaccharide purified from P. alliacea (leaves and stems)—PACO—(25 µg/mL) in presence of polymyxin B. Maturation markers expression was analyzed by flow cytometry showing a mature phenotype in MDDC stimulated with polysaccharide purified from P. alliacea evidenced by increased expression of inductor molecules of immune response such as CD86 and HLA-DR (FIG. 16 panel A and B, respectively). Additionally, TNF-α production was measured by ELISA in a supernatant of MDDC stimulated for 48 h with solvent, LPS and a polysaccharide purified from P. alliacea (leaves and stems)—PACO—(25 µg/mL). FIG. 17 shows an increase in cytokine secretion that correlates with phenotypic maturation observed by flow cytometry.

Example 13

In Vivo Effect of Therapy with Fast Fraction from P. Alliacea and an Immunostimulant Agent $1 \times 10^4$ 4T1 cells were inoculated in the mammary fat pad in 8 female Balb/c mice, after verify development of tumour, mice were treated via IP with bioactive fraction from P. alliacea (2 mg) or control vehicle. Tumour size was determined weekly. Since second week bioactive fraction from P. alliacea were administrated and after 24 h immunostimulant agent at lower doses were inoculated via IP. After 3 weeks, an statistically significant reduce in tumour size was determined in both groups (with and without immunostimulant agent). Proliferative response against tumoural antigens showed that mice treated with immunostimulant agent have a higher proliferation compare to P. alliacea alone treatment.

From results showed herein, it could be established that bioactive fractions from P. alliacea induced cytoskeleton alterations, G2 cell cycle arrest and then apoptosis death with DNA fragmentation. Apoptotic bodies could be phagocytosed by dendritic cells, which will be then activated by immunostimulant agent, allowing tumoural antigen presentation to both CD4 and CD8 lymphocytes, inducing an immune response that control metastasis generated by tumour cells that scape to direct anti-tumoural treatment.

These results allow established that bioactive fractions from P. alliacea have activity over multiple molecular targets available in tumour cells due to compound diversity in fractions, which could act in synergy increasing anti-tumour activity. This fact contrasts with conventional drugs used in chemotherapy regime, which act over a single molecular target, allowing tumour cell to develop a treatment resistance faster than using complex fractions such as claim in present patent application. Additionally, the production costs of fractions herein disclosed is notably lower than required by synthetic drugs production.

The invention claimed is:

1. A bioactive fraction of *Petiveria alliacea* obtained by bioguided procedures, standardized and analytically marked for treating cancer, comprising:

| COMPOUND | % weight respect total bioactive fraction |
|---|---|
| 4-ethyl petiveral | 0.01-5 |
| Lignoceric acid | 0.01-5 |
| Dibenzyl disulfide | 0.01-5 |
| Dibenzyl tetrasulfide | 0.01-5 |
| Dibenzyl trisulfide | 3.8-7 |
| Leridal-7-demethyl | 3.8-7 |
| Leridal Chalcone | 0.01-5 |
| Leridol | 0.01-5 |
| Myricitrine | 0.01-5 |
| Petiveral | 20.6-38.2 |
| Pinitol | 0.01-5 |
| S-benzyl cysteine sulfoxide | 0.01-5 |
| Senfol | 0.01-5 | wherein the bioactive faction decreases clonogenic capacity in tumour cells.

2. A The bioactive fraction of *Petiveria alliacea* obtained by bioguided procedures, standardized and analytically marked for treating cancer according to claim 1, wherein the bioactive fraction comprises the following chromatographic fingerprint in an analysis by HPLC coupled to UV detector at 280 nm using RP-18 column and mobile phase (A) $H_2O$+ formic acid 1% and (B) MeOH+formic acid 0.1% according to the elution gradient –60% solvent A since 0 until 5 minutes, 0% solvent A in 45 minutes and 60% solvent A since 52 until 62 minutes:

| Peak | Retention time (min) |
|---|---|
| 1 | 8.31 |
| 2 | 20.38 |
| 3 | 22.58 |
| 4 | 26.68 |
| 5 | 28.32 |
| 6 | 34.12. |

3. A The bioactive fraction of *Petiveria alliacea* obtained by bioguided procedures, standardized and analytically marked for treating cancer according to claim 1, wherein the bioactive fraction comprises the following chromatographic fingerprint in an analysis by HPLC coupled to PDA detector using RP-18 column and mobile phase H20: CAN (4:6):

| Peak | Retention time (min) | λ (nm) |
|---|---|---|
| 1 | 29.37 | 324 |
| 2 | 33.42 | 265 |
| 3 | 48.27 | 265. |

4. A pharmaceutical composition for treating cancer comprising the bioactive fraction of *Petiveria alliacea* according to claim 1 and at least one or more pharmaceutically acceptable excipients.

5. A kit for treating cancer comprising the first pharmaceutical composition according to claim 4, a second pharmaceutical composition containing one or more immunostimulant agents that can produce the phenotypic and/or functional maturation of the dendritic cells and at least one or more pharmaceutically acceptable excipients and optionally instructions for use.

6. A pharmaceutical combination for treating cancer comprising the bioactive fraction of *Petiveria alliacea* according to claim 1 and at least one immunostimulant agent that can produce the phenotypic and/or functional maturation of the dendritic cells.

7. The pharmaceutical combination for treating cancer according to claim 6 wherein the immunostimulant agent that can produce the phenotypic and/or functional maturation of the dendritic cells is a polysaccharide and/or glycopeptide obtained from: *Ganoderma lucidum, Astragalus membranaceus, Grifola frondosa, Phellinus linteus, Cordyceps militaris, Lentinus edodes, Coriolus vericolor, Agaricus blazei* or *Petiveria alliacea*.

8. A bioactive fraction of *Petiveria alliacea* obtained by bioguided procedures, standardized and analytically marked for treating cancer, comprising:

| COMPOUND | % weight respect total bioactive fraction |
|---|---|
| 4-ethyl petiveral | 0.01-5 |
| Lignoceric acid | 0.01-5 |
| Dibenzyl disulfide | 0.01-5 |
| Dibenzyl tetrasulfide | 5-9.5 |
| Dibenzyl trisulfide | 4.5-8.7 |
| Leridal-7-demethyl | 0.01-5 |
| Leridal chalcone | 19-36 |
| Leridol | 8-15 |
| Myricitrine | 0.01-5 |
| Petiveral | 32-55 |
| Pinitol | 0.01-5 |
| S-benzyl cysteine sulfoxide | 2-5 |
| Senfol | 0.01-5 | wherein the bioactive fraction induces early nonreversible mitochondrial membrane depolarization and decreases Hsp70 expression on tumoural cells.

9. A pharmaceutical composition for treating cancer comprising the bioactive fraction of *Petiveria alliacea* according to claim 8 and at least one or more pharmaceutically acceptable excipients.

* * * * *